US012751725B2

(12) United States Patent
Qadir et al.

(10) Patent No.: US 12,751,725 B2
(45) Date of Patent: Oct. 6, 2026

(54) CRANIAL DRILL WITH AUTOMATIC STOP AND ASSOCIATED SYSTEMS AND METHODS

(71) Applicant: Hubly Inc., Lisle, IL (US)

(72) Inventors: Casey Mimi Qadir, Vienna, VA (US); Nathanael David Andrews, Washington, DC (US); Tyler Panian, Lisle, IL (US); Michael Nagy, Glen Ellyn, IL (US); Amit Bhasker Ayer, Chicago, IL (US); Matthew Ahlbeck, Chicago, IL (US)

(73) Assignee: Hubly Inc., Lisle, IL (US)

( * ) Notice: Subject to any disclaimer, the term of this patent is extended or adjusted under 35 U.S.C. 154(b) by 232 days.

(21) Appl. No.: 18/689,813

(22) PCT Filed: Sep. 7, 2022

(86) PCT No.: PCT/US2022/042807

§ 371 (c)(1),
(2) Date: Mar. 6, 2024

(87) PCT Pub. No.: WO2023/039004

PCT Pub. Date: Mar. 16, 2023

(65) Prior Publication Data

US 2024/0382214 A1 Nov. 21, 2024

Related U.S. Application Data

(60) Provisional application No. 63/241,424, filed on Sep. 7, 2021.

(51) Int. Cl.
*A61B 17/16* (2006.01)
*A61B 17/00* (2006.01)

(52) U.S. Cl.
CPC ...... *A61B 17/1617* (2013.01); *A61B 17/1695* (2013.01); *A61B 2017/00022* (2013.01)

(58) Field of Classification Search
CPC ........................ A61B 17/1626; A61B 17/1617
See application file for complete search history.

(56) References Cited

U.S. PATENT DOCUMENTS 4,359,906 A 11/1982 Cordey
4,936,721 A * 6/1990 Meyer ..................... B23B 51/08 408/230

(Continued)

FOREIGN PATENT DOCUMENTS

| | | |
|---|---|---|
| EP | 2560793 B1 | 10/2014 |
| EP | 2128734 B1 | 4/2015 |

(Continued)

OTHER PUBLICATIONS

ISR/US International Search Report and Written Opinion for PCT International patent application No. PCT/US2022/042807 filed Sep. 7, 2022, mailed Jan. 3, 2023, Applicant: Hubly Inc., 9 pages.

*Primary Examiner* — Christian A Sevilla
(74) *Attorney, Agent, or Firm* — Ashurst Perkins Coie US LLP

(57) ABSTRACT

The present technology relates to surgical drilling devices, and associated systems and methods. In some embodiments, a surgical drilling device includes a drill bit and a drill motor. During operation, the drill bit and the drill motor can generate one or more parameters. The parameters can correspond to the drilling behavior of the drill bit, for example, to a type of tissue or a drill bit penetration depth, such that the parameters can be used to create an automatic stop threshold. In some embodiments, the surgical drilling device can be configured to measure one or more of the parameters, and to automatically stop the drill motor based on a com- (Continued)

parison of the measured parameter(s) and the automatic stop threshold.

37 Claims, 16 Drawing Sheets

(56) References Cited

U.S. PATENT DOCUMENTS

| | | | | |
|---|---|---|---|---|
| 5,876,405 | A | 3/1999 | Del Rio et al. | |
| 7,121,773 | B2 | 10/2006 | Mikiya et al. | |
| 8,511,945 | B2 | 8/2013 | Apkarian et al. | |
| 8,881,842 | B2 | 11/2014 | Borinato et al. | |
| 9,022,949 | B2 | 5/2015 | Herndon | |
| 9,162,331 | B2 | 10/2015 | Tang | |
| 9,345,487 | B2 | 5/2016 | Herndon et al. | |
| 10,245,043 | B2 | 4/2019 | Xie | |
| 10,383,674 | B2 * | 8/2019 | Sexson | A61B 17/1626 |
| 10,471,576 | B2 | 11/2019 | Totsu | |
| 11,090,128 | B2 * | 8/2021 | Pfotenhauer | A61B 17/1626 |
| 11,130,217 | B2 | 9/2021 | Totsu | |
| 11,154,307 | B2 | 10/2021 | Chiang | |
| 2003/0185640 | A1 * | 10/2003 | Ito | B23B 51/02 408/230 |
| 2005/0116673 | A1 | 6/2005 | Carl et al. | |
| 2005/0131415 | A1 | 6/2005 | Hearn et al. | |
| 2009/0245956 | A1 | 10/2009 | Apkarian et al. | |
| 2011/0020084 | A1 * | 1/2011 | Brett | G05B 19/4166 408/1 R |
| 2011/0245833 | A1 * | 10/2011 | Anderson | A61B 17/1628 606/80 |
| 2013/0126202 | A1 | 5/2013 | Oomori et al. | |
| 2014/0239600 | A1 | 8/2014 | Walsh et al. | |
| 2017/0202560 | A1 * | 7/2017 | Björn | A61B 17/1695 |
| 2019/0150954 | A1 | 5/2019 | Xie | |
| 2020/0054410 | A1 * | 2/2020 | Pfotenhauer | A61B 17/1626 |
| 2023/0088846 | A1 | 3/2023 | Laing et al. | |

FOREIGN PATENT DOCUMENTS

| | | | |
|---|---|---|---|
| EP | 2380704 | B1 | 4/2015 |
| EP | 1651374 | B1 | 11/2016 |
| EP | 2913155 | B1 | 10/2021 |
| WO | 2020113144 | A1 | 6/2020 |

* cited by examiner

CRANIAL DRILL WITH AUTOMATIC STOP AND ASSOCIATED SYSTEMS AND METHODS

CROSS-REFERENCE TO RELATED APPLICATION

The present application claims priority to U.S. Provisional Patent Application U.S. 63/241,424, filed Sep. 7, 2021, the entirety of which in incorporated by reference herein.

TECHNICAL FIELD

The present technology generally relates to medical devices and, in particular, to surgical devices and cranial drilling systems including automatic stop mechanisms.

BACKGROUND

Cranial drills are used in a variety of neurological surgeries, including those required for treating effects of head trauma, stroke or aneurysm, hydrocephalus, as well as for biopsy, pressure relief, and insertion of therapeutic or diagnostic devices. In many cases, emergency cranial access must be obtained as quickly as possible to avoid patient death or permanent injury. Cranial drills may be used in or outside of operating rooms at hospitals or clinics, as well as field hospitals, urgent care centers, or ambulances.

Many cranial drills in use today are manually operated, with energy provided by a surgeon turning a mechanical crank or similar mechanism. An example of one such device is the Integra Cranial Access Kit manufactured by Integra Life Sciences of Princeton, New Jersey. Drilling using such manual devices requires significant energy from the surgeon's hands, both in providing a normal force to the drill bit and a rotary force on the drill crank to penetrate the skull. Besides being a relatively slow process, such manually powered drilling can result in imprecise hole direction due to fatigue. Moreover, to avoid damaging a subject's cranial tissue (e.g., the meninges, parenchyma, or other internal tissues), the surgeon must cease applying normal and torsional forces at the instant the drill penetrates the skull. Often the surgeon must choose between the loss of precious seconds in an emergency trepanation or other cranial access procedure by drilling slowly and/or gently and the risk of puncture damage upon skull penetration by drilling quickly and/or forcefully.

BRIEF DESCRIPTION OF THE DRAWINGS

Many aspects of the present technology can be better understood with reference to the following drawings. The components in the drawings are not necessarily drawn to scale. Instead, emphasis is placed on clearly illustrating the principles of the present technology. Furthermore, components can be shown as transparent in certain views for clarity of illustration only and not to indicate that the component is necessarily transparent. Components may also be shown schematically.

DETAILED DESCRIPTION

Figure 1:
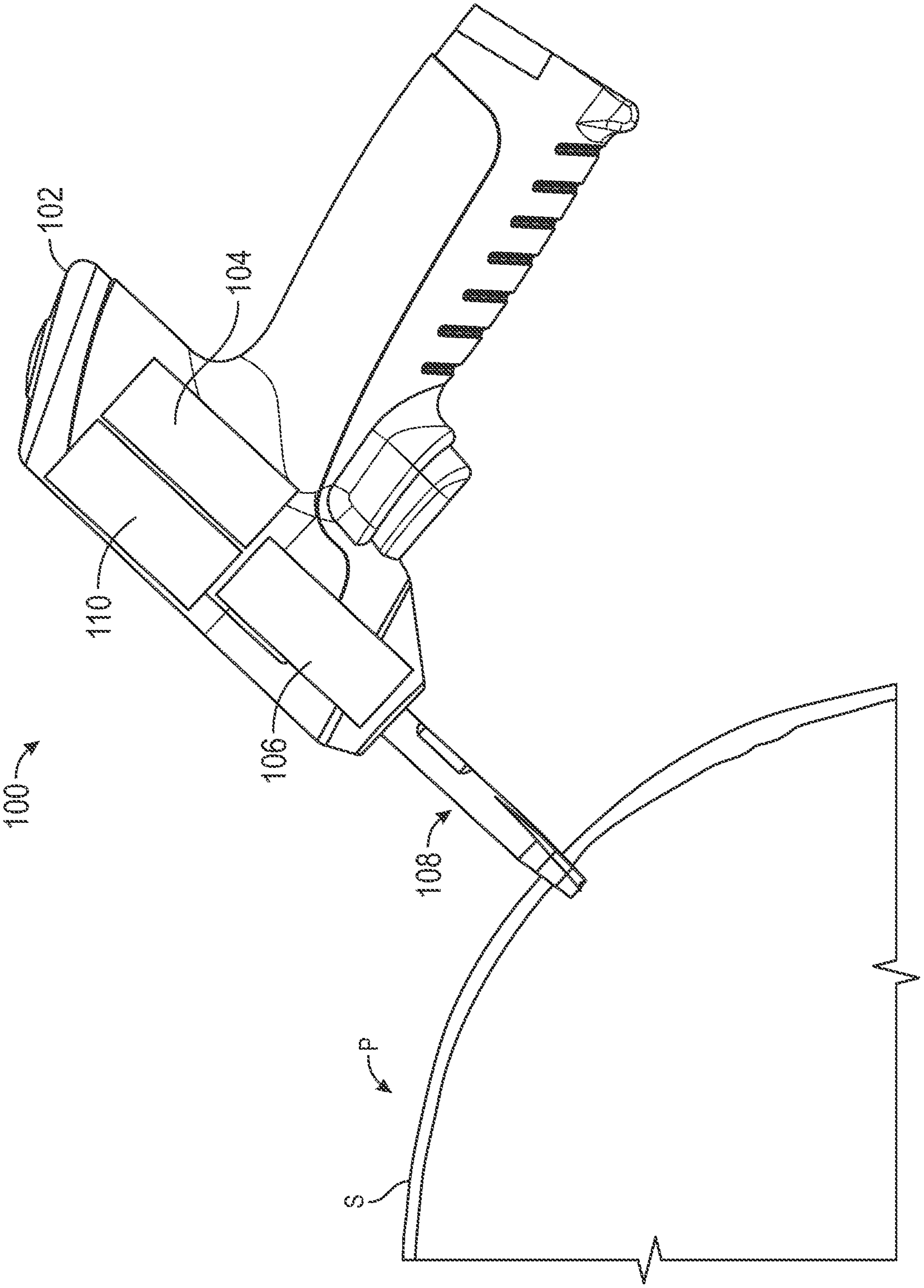
FIG. 1 is a schematic representation of a motorized cranial drilling system configured in accordance with embodiments of the present technology.

The present technology is directed to automatic stop mechanisms for cranial drills. These include various mechanisms for triggering automatic stop, including mechanical clutches, pressure sensors, torque sensors, speed sensors, and motor current sensors. In general, drilling systems in accordance with embodiments of the present technology may including a sensing element configured to sense one or more parameters that provide a repeatable, clearly recognizable signal at or near the moment of penetration into and/or through a drilling surface, such as the patient's skull. The signal can rapidly trigger an autostop mechanism configured to stop the drill motor or retract the drill bit at or near the moment the drill bit penetrates the skull. In some embodiments, the sensing element, motor, and/or bit can be designed or optimized to create or enhance the repeatability and/or recognizability of the sensor signal. In at least some embodiments, for example, the drilling system can include a tapered drill bit having an elongated cutting surface and, in operation, one or more parameters of the drilling system can have a unique (e.g., repeatable, recognizable, etc.) signature corresponding to behavior of the drilling system induced by the interaction between the tapered drill bit and a patient's skull. This signature can be used to develop one or more triggers or thresholds for automatically stopping the drill motor.

Many autostop mechanisms of existing devices are manually adjusted based on, for example, the thickness of a patient's skull, and may involve surgeon setting the autostop mechanism by measuring a length on the drill bit corresponding to the patient's skull thickness. In some instances, surgeons can estimate the patient's skull thickness based, for example, on CT scan results. However, because human skull thicknesses can vary by age, sex, and race, the inventors have discovered that it can be difficult to accurately estimate a given patient's skull thickness. Moreover, CT scan machines are not always available to surgeons when needed, and obtaining CT scan results may require too much time. The current operating room or bedside devices that rely on a manually adjusted drill bit autostop mechanism, such as the Integra Cranial Access Kit manufactured by Integra LifeSciences of Princeton, New Jersey, the Phasor manufactured by Phasor Health of Houston Texas, and the Easy-Drill manufactured by Micromar of Brazil, may trigger at improper times or may fail to properly trigger at skull penetration because these autostop mechanisms generally have designs that lack repeatable, reliable triggering events.

In contrast to these and other drilling systems, drilling systems configured in accordance with embodiments of the present technology are expected to trigger in a more accurate manner, and avoid triggering before the skull is penetrated (false positive) and/or failing to trigger after the skull has been penetrated (false negative). Thus, drilling systems in accordance with embodiments of the present technology can have increased reliability compared to other drilling systems. Some drilling systems include such sensors and, at a preset threshold, are configured to trigger autostop. However, the inventors have determined that many situations occurring during trepanations and/or other cranial access procedures can cause these sensed parameters to cross the preset thresholds, thereby leading to improper triggering. For example, if a user manually reduces normal force on the drill prior to skull penetration, this could reduce tip pressure, motor current, and/or tip torque, as well as increase drill speed. The inventors determined that any of these changes in sensed signals could cross a sensor threshold and cause autostop before the tip fully penetrates the skull. In other instances, the inventors have determined that, if the user changes the angle of normal force manually at the moment of skull penetration, the mechanical load on the drill tip might increase and cause the sensor system to fail to trigger autostop.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but are not described in detail with respect to FIGS. 1-15.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "generally," "approximately," "substantially," and "about" are used herein to mean the stated value plus or minus 10%.

Although certain embodiments herein are described in the context of surgical procedures performed on the skull, this is not intended to be limiting, and a person of ordinary skill in the art will appreciate that the present technology can be applied equally to surgical procedures performed on other parts of the body (e.g., the spine, hip, shoulder, or other orthopedic treatment sites). In at least some embodiments, for example, the present technology can include automatic stop mechanisms for a spinal drill, an orthopedic drill, an orthodontic drill, a bone drill, and/or any other suitable medical drill or tissue-penetrating device. Additionally, although some embodiments are discussed with reference to treatment of hydrocephalus, the present technology can be readily adapted for treatment of other indications, such as subdural hematomas, epilepsy, intracranial hemorrhage, stroke, traumatic brain injury, cancers of the nervous system, brain tumors, spinal fusion, vertebroplasty, kyphoplasty, hip replacement, shoulder arthroplasty, rotate cuff repair, SLAP repair, humeral fracture surgery, knee replacement, and/or any other suitable orthopedic indications. Moreover, although certain embodiments are described in terms of a trepanation procedure, such as for placing an EVD, the present technology can also be used in other procedures, such as shunt placement, craniotomy, deep brain stimulation, deep brain electrode placement, minimally invasive catheter evacuation followed by thrombolysis (MISTIE), cooling for acute ischemic brain damage (COOL AID), Ommaya reservoir placement, laser thermal ablation therapy, lumbar puncture, spinal tap, or brain-machine interfaces.

FIG. 1 illustrates a schematic representation of a motorized cranial drilling system 100 ("drill 100"), configured in accordance with embodiments of the present technology. The drill 100 can include a housing 102 that can contain internal electronic 104, a motor 106 (e.g., a drill motor, a rotary motor, and/or the like), and a drill bit 108. In some embodiments the drill 100 can include one or more sensing elements 110. Although the sensing elements 110 are illustrated as being positioned exterior to the housing 102 in FIG. 1, in other embodiments one or more of the sensing elements 110 can be positioned at least partially within an interior of the housing 102 or at any other suitable position on and/or at least partially within the drill 100. As discussed in greater detail below, each of the sensing elements 110 can be configured to sense one or more parameters ("the drill parameters") associated with the drill 100 and/or the operation thereof. Individual ones of the sensing elements 110 can be operably coupled to the electronics 104, and the electronics 104 can be operably coupled to the motor 106. Accordingly, based at least partially on the one or more parameters sensed by the sensing elements 110, the electronics 104 can cause the motor 106 to stop (e.g., automatically stop or "autostop") the bit 108 and/or retract the bit 108. For example, the electronics 104 can be configured to stop the bit 108 once the bit 108 has penetrated, or is close to penetrating, a skull S of a patient. Stopping the bit 108 at or near skull penetration automatically is expected to reduce or prevent damaging the patient's cranial tissues. In operation, the drill 100 can be held and/or guided by an operator (e.g., an operator's hand) to carry out trepanation, with the motor 106 controlled by the electronics 104 and configured to be started and stopped based at least partially on the sensing elements 110.

Figure 2A:
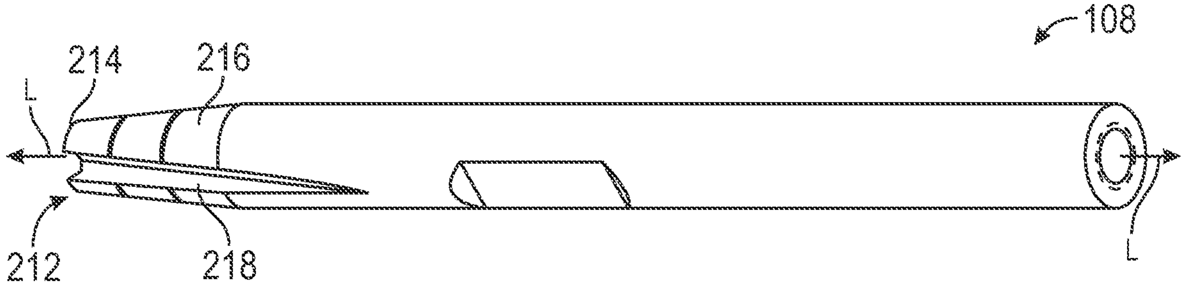
FIGS. 2A-2C are perspective, side, and side cross-sectional views of a drill bit in accordance with embodiments of the present technology.
Figure 2B:
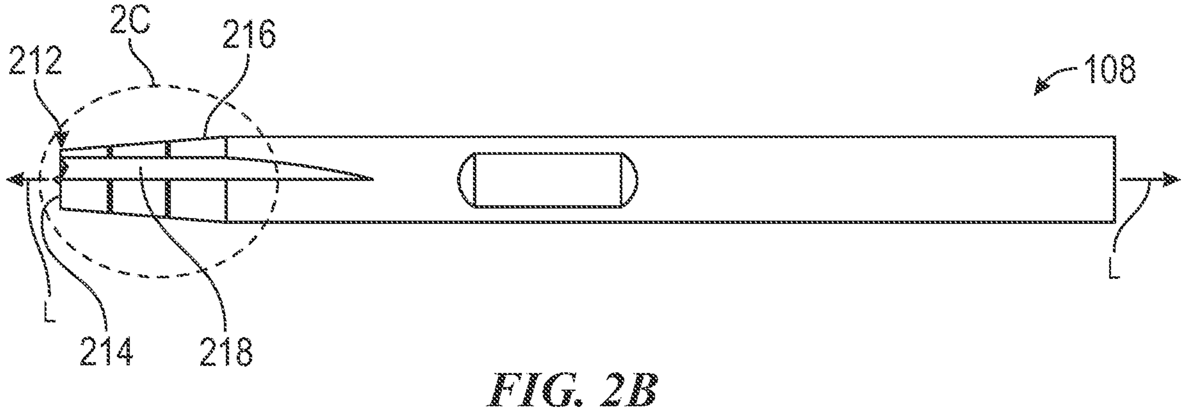
Figure 2C:
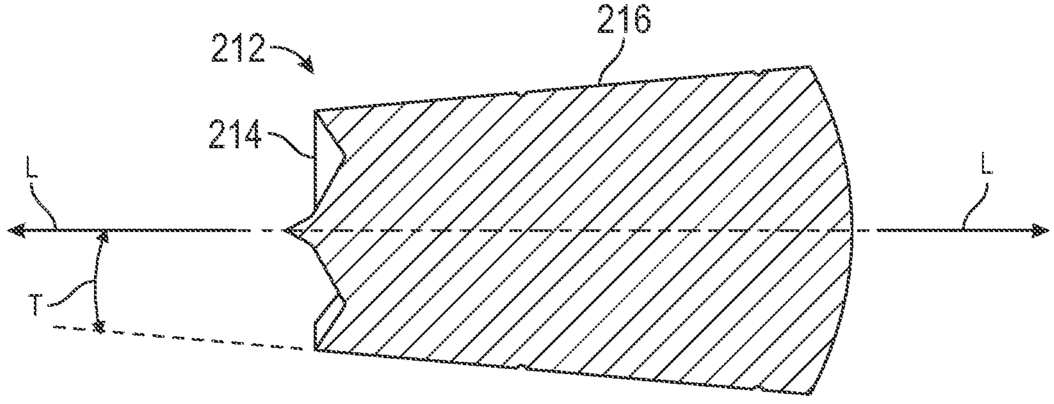

FIGS. 2A and 2B are perspective and side views, respectively, of the drill bit 108 of FIG. 1, in accordance with embodiments of the present technology. FIG. 2C is a cross-section view of region 2C of FIG. 2B. Referring to FIGS. 2A-2C together, the drill bit 108 can include one or more cutting surfaces 212. In the illustrated embodiment, the cutting surfaces 212 include a cutting tip 214 and a cutting sidewall 216. The cutting tip 214 can define a distalmost tip or terminus of the drill bit 108. The cutting sidewall 216 ("sidewall 216") can extend proximally from the cutting tip 214 and radially outward to define an angle or taper T (labeled in FIG. 2C) relative to a longitudinal axis L of the drill bit 108. In the illustrated embodiment, the taper T is 5-degrees. In other embodiments, the taper T can be between about 0 degrees and about 15 degrees, such as at least 1 degree, 2 degrees, 3 degrees, 4 degrees, 10 degrees, or any other suitable angle therebetween. In further embodiments, the taper T can be any suitable angle up to 90 degrees. In these and other embodiments, the shape of the taper T can correspond to or be different than a cross-sectional shape of the drill bit 108. In the illustrated embodiment, for example, the drill bit 108 has a circular cross-sectional shape and the taper T has a correspond conically-shape. In other embodiments, the taper T can have other suitable shapes.

Referring again to FIGS. 2A and 2B, the drill bit 108 can include one or more flutes 218. Individual ones of the flutes 218 can a linear shape and/or extend proximally from the cutting tip 214, for example, in a direction at least generally parallel to the longitudinal axis L. For example, in at least some embodiments the flutes 218 are not helical shaped and/or do not extend radially around a portion of the longitudinal axis L. During a drilling procedure, the linear shape of the flutes 218 is expected to inhibit or prevent unintentional movement of the drill bit 108, such as if one or more of the flutes 218 catches on the skull S (FIG. 1). For example, compared to helically-shaped flutes, which can cause drill bits to advance unintentionally when caught on drilling substrate and may result in harm to the patient's cranial tissues, the linear shape of the flutes 218 is expected to advance the drill bit 108 if one or more of the flutes 218 catch on the skull S (FIG. 1) during drilling.

Figure 3A:
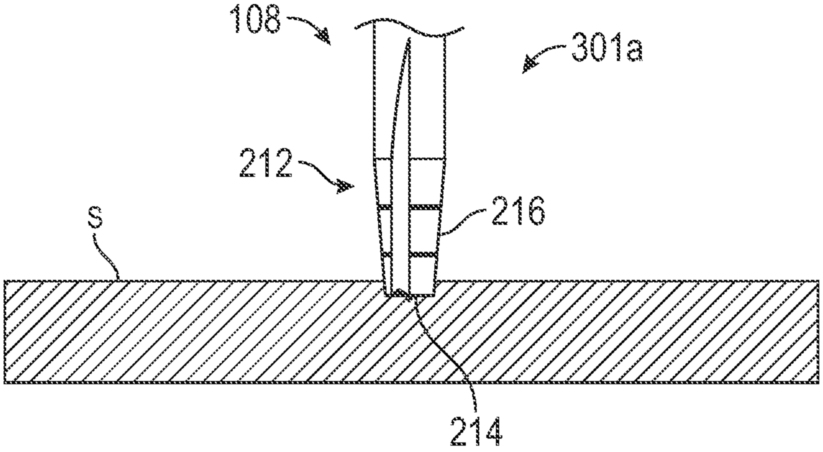
FIGS. 3A-3C are side views of the drill bit of FIG. 2A-2C at various stages of a drilling process, in accordance with embodiments of the present technology.
Figure 3B:
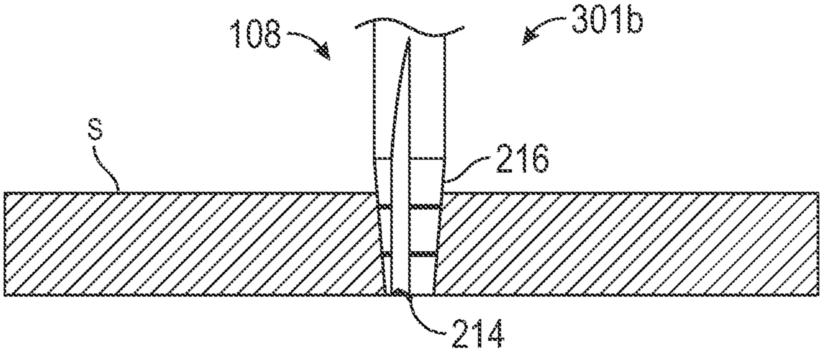
Figure 3C:
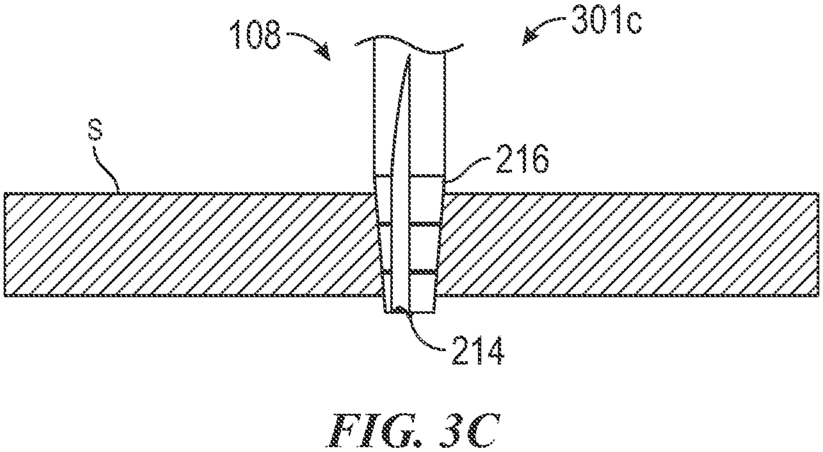

FIGS. 3A-3C are side views of the drill bit 108 at various stages 301*a-c* of a drilling process, in accordance with embodiments of the present technology. More specifically, FIG. 3A illustrates the drill bit 108 at a first or pre-penetrated stage 301*a* of the drilling process in which the drill bit 108 has begun to cut into the skull S, FIG. 3B illustrates the drill bit 108 at a second or partially penetrated stage 301*b* in which at least a portion of the drill bit 108 (e.g., the cutting tip 214) begins to penetrate through the skull S, and FIG. 3C illustrates the drill bit 108 at a third or fully-penetrated stage 301*c* in which the drill bit 108 has penetrated through the skull S.

Figure 4A:
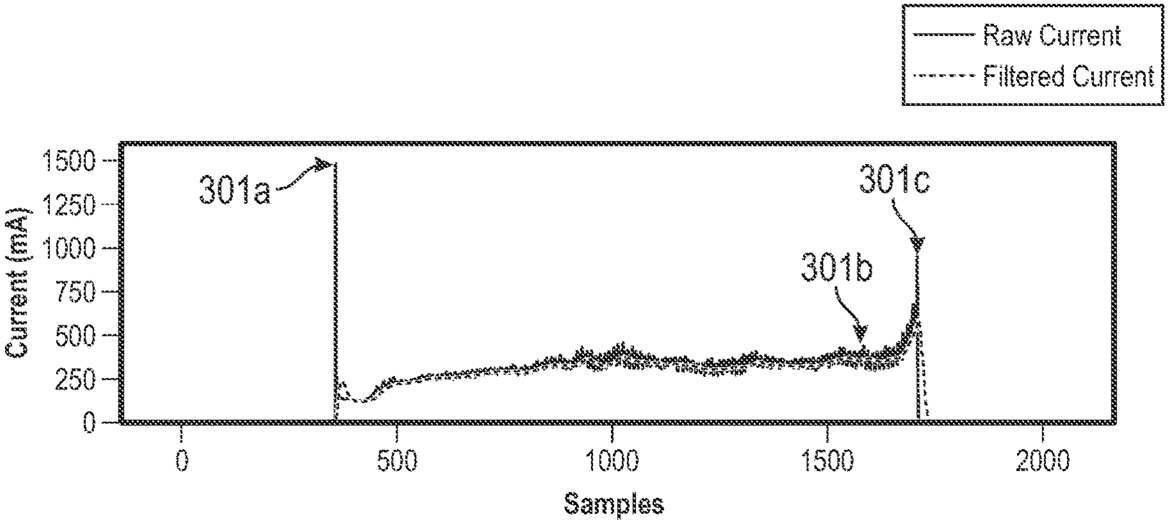
FIGS. 4A-4C are lines plots of current, a first derivative of the current, and a second derivative of the current, respectively, during a drill process, in accordance with embodiments of the present technology.
Figure 4B:
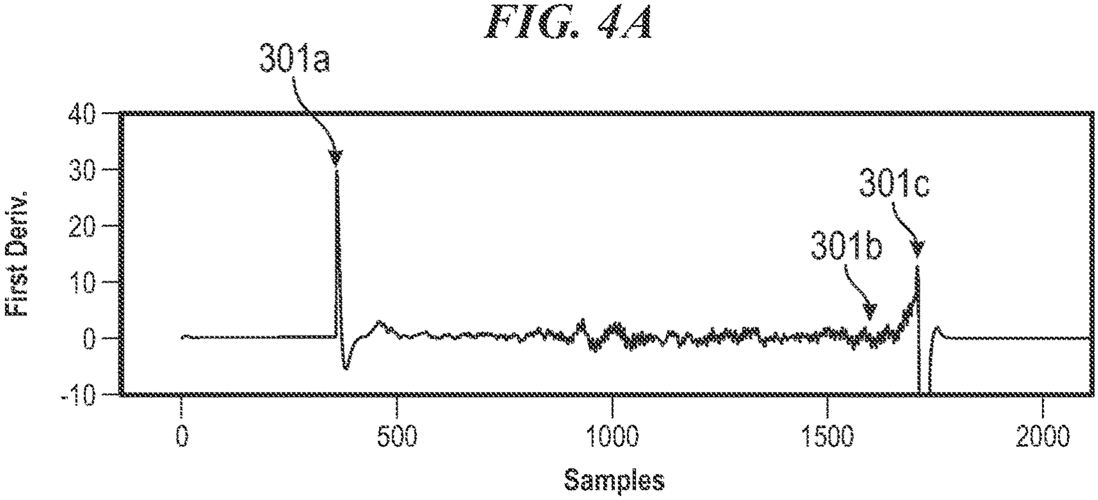
Figure 4C:
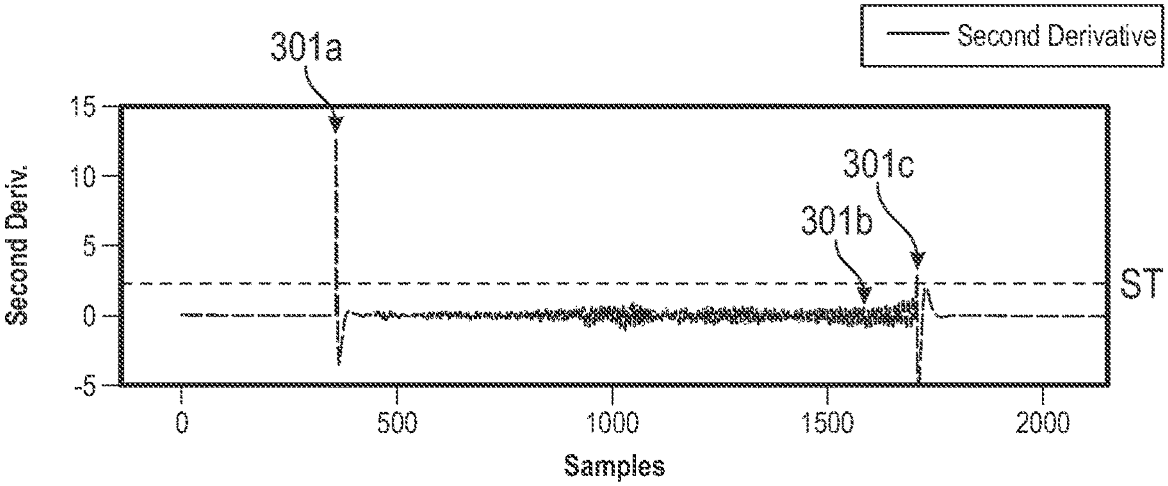

During a drilling procedure, the cutting surfaces 212 of the drill bit 108 are configured to cause or evoke the parameters at which the drill 100 (FIG. 1) is configured to stop drilling. Accordingly, during one or more of the stages 301*a-c,* one or more of the drill parameters can be measured (e.g., by the drill 100 and/or the sensing elements 110, FIG. 1) to monitor the penetration/drilling depth of the drill bit 108 and/or determine when to stop the drill bit 108. For example, current drawn by the motor 106 to drive the drill bit 108 during the drilling process can be measured and used to determine when to stop the drill bit 108. One such example is shown in FIGS. 4A-4C, which are lines plots of current, the first derivative of the current, and the second derivative of the current, respectively, before, during, and after each of the stages 301*a-c* described with reference to FIGS. 3A-3C. In FIGS. 4A-4C, the data has been low-pass filtered, and each of the first and second derivatives have been determined using a point-by-point subtraction method (e.g., to calculate the change in current between two points in time). In other embodiments, the data can be unfiltered or filtered using another suitable technique, and/or one or both of the first and second derivatives can be determined using another suitable technique.

Referring to FIGS. 3A-4C together, the amount of current drawn by the motor 106 is expected to vary based at least partially on the penetration/drilling depth of the drill bit 108. Changes in the amount of current drawn, such as shown in the plot of the first derivative (FIG. 4B) or the second derivative (FIG. 4C), can be used to determine when to stop the drill bit 108. For example, as the cutting tip 214 advances further into and/or through the skull S, such as during the first and/or second stages 301*a,* 301*b,* the contact between the sidewall 216 and the skull S can increase, which can result in a corresponding increase in resistance to rotation of the drill bit 108 and cause the drill motor 106 to draw increased amounts of current in response. This is shown, for example, in FIGS. 4A-4C in the increase in current between the first stage 301*a* and the third stage 301*c.* At the third stage 301*c,* the drill 100 can be configured to inhibit or prevent further rotation of the drill bit 108, such as by shutting off power to the motor 106 and/or reversing power to the motor 106 to cause the drill bit 108 to rotate in a opposite direction. Referring to FIG. 4C, for example, when the second derivative of the current reaches or exceeds a stop threshold ST associated with the penetration of the drill bit 108 through the skull S in the third stage 301*c,* the drill 100 can be configured to stop providing current to the motor 106 to inhibit or prevent further rotation of the drill bit 108.

The change in current associated with the stop threshold ST can be based at least partially on the change in resistance to movement and/or rotation of the drill bit 108 before, during, and/or after one or more of the stages 301*a-c*. For example, when the cutting tip 214 initially breaks through the skull S at the second stage 301*b,* the change in contact between the drill bit 108 and the skull S can cause a corresponding change (e.g., a decrease) in the resistance to movement of the drill bit 108 through the skull S, at least because the cutting tip 214 is no longer in contact with the skull S. However, even after the cutting tip 214 penetrates through the skull S, the tapered shape of the sidewall 216 can cause mechanical interference with the skull S to inhibit or prevent further insertion of the drill bit 108 through the skull S. As described in further detail below with reference to FIG. 5A, the change (e.g., decrease) in resistance to movement/rotation of the drill bit 108 can alter the operation of the drill motor and cause a corresponding change (e.g., increase) in the current drawn by the motor. This change in the current can correspond to a positive acceleration of the current drawn by the motor. The current draw can continue to increase (e.g., accelerate) up until the third stage 301, at which point the second derivative of the current can be equal to or exceed the stop threshold ST and operation of the drill can terminate.

Figure 5A:
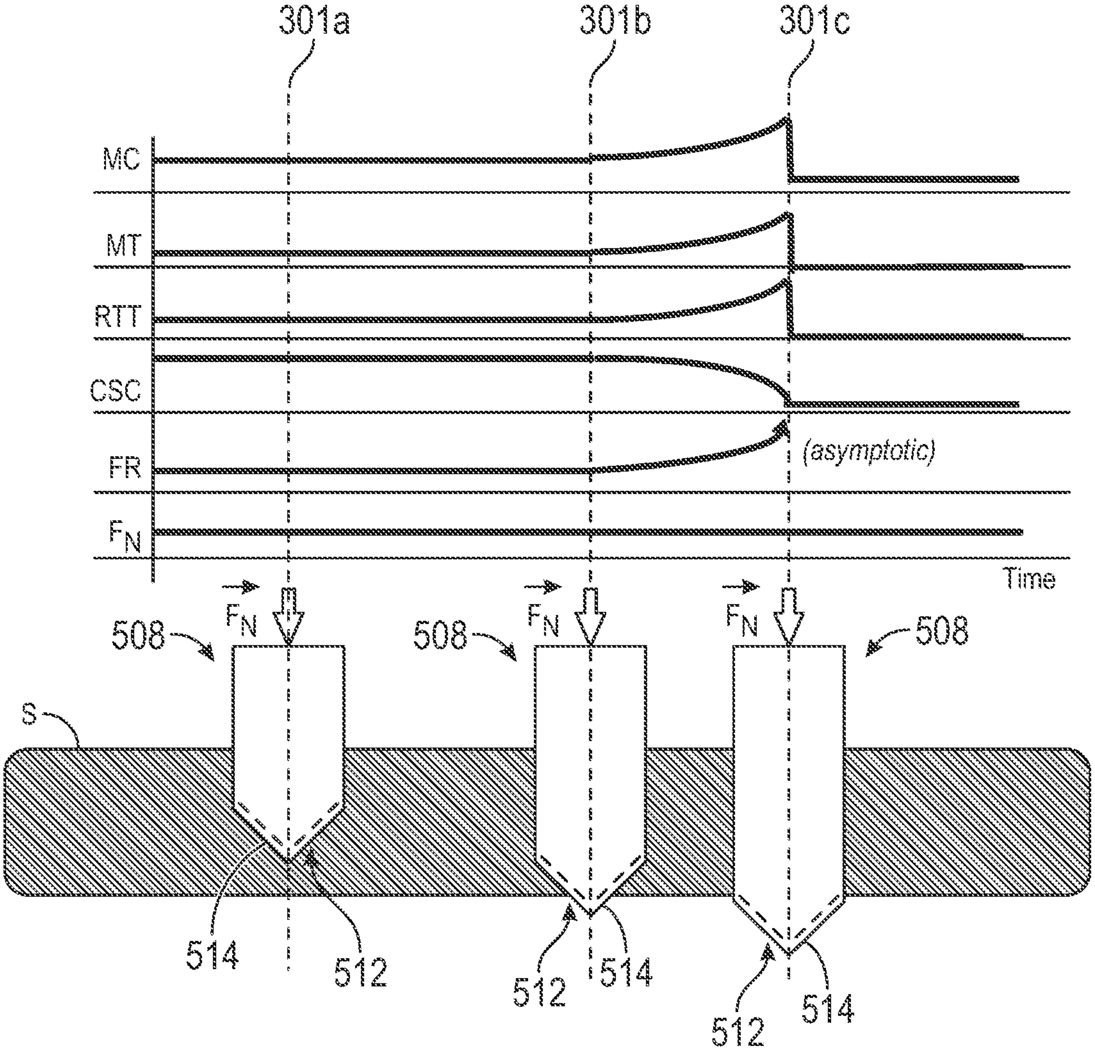
FIG. 5A illustrates the transient behavior of various drill parameters before, during, and after skull penetration, with a constant Normal Force applied, in accordance with embodiments of the present technology.

FIG. 5A depicts several drill parameters that can be measured during the drilling process, in accordance with embodiments of the present technology. FIG. 5A further includes line plots based on the inventors' investigation of drilling in bone and autostop functionality for drills configured to apply a generally constant normal force $F_N$ when drilling. The line plots of FIG. 5A illustrate the characteristic trends of several parameters over time, including at the stages 301*a-c*. In the illustrated embodiment, the drill parameters include:

- Normal Force $F_N$: linear force on a drill bit 508 in the direction of the bit's longitudinal or rotational axis, which is generally or substantially perpendicular to the skull surface.
- Feed Rate FR: the linear velocity at which the bit 508 progresses into the skull S in the direction of normal force $F_N$.
- Cutting Surface Contact CSC: the total length of contact between the bit's cutting or drilling surface(s) 512 and the skull S. Cutting surfaces 512 of a drill bit can include cutting tip 514, such as the surface(s) symbolized in FIG. 5A by dashed lines.
- Resistance to Torque RTT: The mechanical opposition from the skull bone S to torque created by the rotary motor. It is coupled from the skull to the motor via the cutting surfaces 512 of the bit 508 and the bit's shaft.
- Motor Torque MT: mechanical torque provided by the motor 106.
- Motor Current MC: electric current drawn by the motor 106 at constant motor voltage MV. Although FIG. 4 illustrates the current characteristic of a DC motor, the same general shape would apply to an AC motor's total RMS current.

In the drill 100 illustrated in FIG. 1, the operator can manually provide the normal force $F_N$, for example, by pressing the drill bit 108 against or toward the skull bone S of a subject. In FIG. 5A the normal force $F_N$ is held constant before, during, and after each of the stages 301*a-c*. However, it can be appreciated that in practice, an operator (e.g., a surgeon) may manually reduce the normal force $F_N$ to zero after penetration in the third stage 301*c*, for example, to avoid injuring the patient. Thus, the illustrated case is intended only to illustrate aspects of the present technology and should not be construed as a limitation or requirement.

Between the first stage 301*a* and the second stage 301*b*, the feed rate FR is expected to remain constant if the normal force $F_N$, the skull resistance to torque RTT, and the motor voltage MV remain constant. However, once the drill bit 508 nears or begins to penetrate through the skull bone S, such as at the second stage 301*b*, the cutting surface contact CSC is expected to decrease as at least a first portion of the cutting surfaces 512 (e.g., the cutting tip 514) has reduced contact with and/or is no longer in contact with the skull S. The drill bit cutting surfaces 512 are expected continue to cut through a same volume of skull material per unit time. As long as the normal force $F_N$ remains constant, keeping cut volume constant can include increasing the feed rate FR. As seen in FIG. 4, the decrease in the cutting surface contact CSC can correspond to or coincide with an increase (e.g., an asymptotic increase) in the feed rate FR up to and/or until the third stage 301*c*. During the third stage 301*c*, the feed rate FR becomes infinite if the normal force $F_N$ is not reduced. Since the cutting surface contact CSC length decreases but the total bone volume cut remains constant, the motor is expected to perform more work with each cutting rotation of the bit and therefore experience increased resistance to torque RTT. The drill electronics can be configured to respond to the rising resistance to torque RTT by drawing more motor current MC to maintain the constant motor voltage MV, as illustrated in FIG. 5A by the increase in the Motor Current.

From a work (physics) perspective, between the first stage 301*a* and the second stage 301*b*, a point on the cutting surfaces 512 travels downward in a generally helical or circular path, driven by motor rotational torque and the normal force $F_N$. at the second stage 301*b*, the reduced cutting surface contact CSC is expected to produce a corresponding reduction in total friction resistance to rotation of the drill bit. The motor and normal force $F_N$ can continue to perform the same work per motor rotation/revolution, so the cutting surfaces 512 are expected to move an increased linear distance per rotation, for example, to maintain the energy balance of the drilling system. Thus, the total distance traveled by the cutting surfaces 512 per rotation is expected to increase when the drill bit is at or near the initially-penetrate stage 301*b*, which is expected to produce a corresponding increase in the amount of input energy (e.g., the motor current MC) drawn by the motor. The motor can be configured to compensate for the additional energy. Generally, the motor is configured to cause rotational movement of the drill bit 508, and, because the drill bit 508 has a fixed circumference, the rotational distance traveled by the drill bit 508 does not change in response to the increased energy drawn by the motor. Accordingly, to increase its work input, the motor can be configured to increase the motor torque MT, as illustrated in FIG. 5A by the increase in the motor torque T at and/or after the initial penetration in the second stage 301*b*. Put differently, the reduction of the cutting surface contact CSC can reduce the work input by the normal force $F_N$, and the drill can be configured to compensate by increasing the work input in the rotational direction by the motor. With motor voltage MV held constant by the electronics, the increase in work input per motor rotation can result in an increase in input current, as illustrated, for example, by the increase in the motor current MC in FIG. 4. Once full skull penetration occurs in the third stage 301*c*, the cutting surface contact CSC can decrease (e.g., to zero, causing the resistance to torque RTT, which had been increasing with the rising feed rate FR and the reduced cutting surface contact CSC, to also drop to zero. The constant voltage regulator in the drill's electronics section can be configured to reduce the motor current MC and hence the motor torque MT to match the new zero resistance to torque RTT.

In the illustrated embodiment, the drill bit 508 does not include the tapered sidewall 216 of the drill bit 108 of FIGS. 2A-2C. In embodiments including the tapered sidewall 216, however, the resistance to torque RTT would not drop to zero but instead to a non-zero value associated with the mechanical interference/resistance to further insertion due to the tapered sidewalls, as described previously with reference to FIGS. 3A-4C. Accordingly, in such embodiments, the drill's electronics can be configured to reduce the motor current MC and hence the motor torque MT to match the new non-zero resistance to torque RTT. Furthermore, a person of ordinary skill in the art will recognize that the operation of the drilling system, as represented by the parameters in FIG. 5A, is idealized and that, in practice, the motor torque and the motor current Mc may not go to zero but instead transition to their respective no-load values, such as the no-load values defined by the motor and the bit's internal mechanical friction and/or electrical characteristics. Additionally, in some embodiments the operator of the drilling system may have to manually stop applying a normal force $F_N$ to the drilling system to bring the feed rate FR to zero.

At least one of the characteristic parameters considered in FIG. 5A, such as the motor current MC, can be used to create a drill system with improved autostop characteristics. Because the parameters are associated with general operational attributes/characteristics of drill systems, the parameters can be used to establish one or more generally applicable thresholds that can be used repeatedly, such as with one or more patients and/or one or more clinical applications. In some embodiments, the drilling system can include a sensor configured to sense the motor current MC during drilling, such that the drilling system can sense the increased current draw by the motor described previously and with reference to FIG. 5A, and trigger an autostop mechanism to stop the drill motor and/or retract a drill bit at or before full penetration in the third stage 301*c*. The stop threshold ST described previously with reference to FIGS. 3A-4C is another example of a threshold for triggering an autostop mechanism. In at least some embodiments, the current drawn by the motor can represent a first threshold for triggering an autostop mechanism, and one or more other thresholds (e.g., a second threshold) can be used in addition to the first threshold. The additional thresholds can relate to different performance parameters than that of the first threshold and can be used to confirm or verify that the autostop mechanism should be triggered to stop rotation of the drill bit. Each threshold can be associated with one or more values and/or value ranges of a corresponding parameter of the drill motor, such as any of the parameters described herein. Further examples that can be implemented in drilling systems of the present technology are described in detail below.

Sensing circuits and/or components, such as the sensing elements 110 configured to measure the characteristic parameters and described previously and with reference to FIG. 1, can include, for example, one or more capacitive pressure sensors, inductive pressure sensors, capacitance measuring circuits, thermistors, torque sensors, strain gauges, load cells, proximity sensors, distance sensors, position sensors, or any other suitable sensing elements known to those of skill in the art. In some embodiments, sensing of surrogates for changing current can include one or more magnetic field sensors, hall effect sensors, voltage across shunts, fluxgate magnetometers, and/or any other suitable current change and/or current change surrogate sensing element. In some embodiments the sensing elements can include one or more L18P D15-OP current sensors manufactured by Tamura Inc, of Tokyo, Japan, one or more current sensors built into a motor driver chip, such as the DRV8885 by Texas Instruments, of Dallas TX, and/or any other suitable sensing element and/or configuration of sensing element(s). Normal force $F_N$ sensors can include resistive, capacitive, plunger, ball, membrane, strain gage and load cell types, including, for example, the 32311096 FSA series force sensor by Honeywell International, of Charlotte, NC. Load cells, such force sensors or strain gages, can include, for example, the 187UV by Vishay Precision Measurement, of Malvern. PA, and may be employed to measure torque or the resistance to torque RTT. Drill cutting surface contact with or proximity (e.g., to different skull layers or meninges) may be detectable with contact or proximity detection circuitry connected to isolated electrical nodes on the drill surface, including, for example, the MTCH101 proximity sensor by MicroChip Corporation, of Chandler, AZ. Motor or shaft speed may also be determined based at least partially on one or more proximity sensors, and/or optical sensors, such as the IS31SE5000 by Lumissil Inc, of Milpitas, CA. Alternatively, processor or analog differentiation circuitry could determine the rate of change with time for any of these parameters. For example, the processor could use a current sensor input to calculate dI/dt or the second time derivative of current $d^2I/dt^2$. In such implementations, the processor can trigger a motor autostop or bit retraction based on one or more of the current I, the rate of current change dI/dt, or the second time derivative of current $d^2I/dt^2$. Time derivatives of any other sensed parameter, or derivatives of any parameter relative to any other parameter, may also be used to influence autostop or any other drill operation.

Any of the parameters described herein, including those described previously and with reference to FIGS. 4A-5A, can be used to establish an autostop threshold. In at least some embodiments, for example, the threshold can include at least one of the current I, the first time derivative of current dI/dt, or the second time derivative of current $d^2I/dt^2$, such as described with reference to FIGS. 4A-4C. The threshold may be a threshold value or range for one of these parameters, or a threshold profile that takes into account one or more changes or variations in the parameters, such as, for example, a change between a positive rate and a negative rate (or vice versa) in dI/dt or $d^2I/dt^2$. In some embodiments, the threshold profile may include more than one change, such as a first change in a first parameter (e.g., I) and a second change in a second parameter (e.g., dI/dt). In some embodiments, the threshold may be a rate of change of one parameter with respect to at least one of the other measured parameters. In some embodiments, the threshold profile may include one or more waveshape features measured or otherwise determined over time. The waveshape feature(s) may include a current amplitude, a number of peaks, a number of waveform notches, or any other suitable waveshape feature. The waveshape feature threshold criteria may be an absolute criterion or value or may be relative to one or more other features in the wave (e.g., the number of peaks having a predetermined current amplitude, etc.).

In one embodiment, changes in current amplitude may be detected as the drill penetrates one or more layers or tables of the skull bone, such that different current levels can correspond to one of the layers. In at least some embodiments, for example, a first current level corresponds to drilling through the hard outer table, a second current level corresponds to drilling through the relatively soft diploe (middle) layer, and a third current level corresponds to drilling through the inner (hardest) table. In some embodiments, the drill may only trigger autostop when passage through all the layers is detected sequentially, for example, when the drill detects the first, second, and third current levels in sequence. In some embodiments, the drill may slow drill speed when the inner table is entered (e.g., as detected by the corresponding third current level), as penetration is likely to occur soon. In some embodiments, based on the current levels, the drill may provide an indication to the operator when one or more of the skull layers is reached. In some embodiments, the one or more sensing element 110 (e.g., the contact sensor(s), the proximity sensor(s), etc.) may be used to identify one or more of the layers, alone or in combination with the current level or any other suitable parameter.

In another embodiment, the drilling system triggers autostop based on a sudden reversal of current or a time derivative (of any order) of current at the moment of final penetration C. In one specific implementation, the system determines the second derivative of current with respect to time, using either digital or analog circuit methods, and includes a mechanism configured to trigger autostop when a time derivative (first or higher order) of current=0. This can, for example, include analog-to-digital conversion and sampling of motor current. Samples may be sent to an internal processor programmed to: compare values to preset thresholds, calculate time rate of change of the current, and/or mathematically compare the values or time rates of change to thresholds or to reference current wave shapes. Further, the processor may remove noise from the data using averaging techniques. Although described with reference to the motor current in other embodiments the drilling system may use one or more of the other measured parameters described herein.

In some embodiments, one or more reference wave shapes, thresholds, or wave features ("the references") are pre-loaded into the device's memory before the procedure. The references may be determined by measurement of actual current draw in a statistically relevant number of human, animal, or artificial models. There may be a plurality of reference current profiles for different skull phenotypes, for example based on age, skull size, skull thickness, or other physiological parameters. The device may have a data interface that allows the operator to input relevant parameters for a given patient, allowing the device to select the appropriate reference. The operator may use medical imaging tools (fluoroscopy, CT scan, MRI, etc.) to determine the relevant parameters prior to the surgery.

Other embodiments may include a spring-loaded rod built into the drill bit tip's point. The rod may extend back through the bit into the body of the drill, the rod coupled to a spring configured to push the rod out of the drill bit towards the skull. Prior to skull penetration in the first stage 301*a*, the normal force $F_N$ compresses the spring as the rod is pushed against the skull. Once the skull is penetrated in the second stage 301*c*, there is no skull to oppose the rod and the spring allows the rod to extend slightly (for example 1-5 mm) out of the bit, before its extension is limited by a built-in mechanical stop. The forward movement of the rod may trigger (e.g., via a contact switch, a proximity sensor, a strain gauge, and/or any other suitable sensing element) an electronic indicator that skull penetration has occurred. This indicator may stop or slow the motor, or provide an audible, visual, and/or haptic signal to the user. The indicator may also be input into an algorithm to determine whether system behavior should change, for example, whether the drill should stop drilling and/or at least partially retract the drill bit. In some embodiments, the rod and spring may be built directly into the bit. Additional and alternative features of retraction mechanisms that can be used in conjunction with the technology disclosed here are shown and described in PCT Patent Application No. PCT/US21/20928, the entirety of which is hereby incorporated by reference.

With continued reference to FIG. 5A, the drilling system may include a device configured to record and save the current profile for upload after the procedure is complete. Uploading may be accomplished by any of the wired or wireless means known in the art and may be automated or may require action by the operator. Uploading can include, for example, activating a control on the device, connecting it to a computer and transferring to a designated cloud database, or physically mailing the device to a designated address. The device manufacturer can maintain a database of all drill current profiles obtained in the field and use this growing database to improve the reference waveform data built into future units. The device manufacturer may request certain patient information from the operator to improve the specificity of the database. The database may be maintained, and the reference waveforms improved upon, using artificial intelligence, including machine learning algorithms, as described in greater detail below.

In a further embodiment, the drilling system slows down motor torque, for example, by reducing motor voltage in the second and/or third stages 301*b*, 301*c*. This slows down both bit rotation, reduces motor torque, and reduces feed rate, all of which serve to increase the time from initial to final penetration, and reduce the risk of pushing the bit deeper into the cranium at full penetration in the third stage 301*c*. In some implementations of this embodiment, the system changes autostop current thresholds at the moment of initial penetration in the second stage 301*b*, in order to account for the reduced motor speed, motor torque, and feed rate. As described above, in another embodiment the system slows down earlier, for example when it detects penetration of the inner table layer.

In some embodiments, the drill bit point is configured to alter or accentuate one or more of the parameters. In at least some embodiments, for example, the drill bit point can be dimensioned or shaped to create a unique and easily recognizable (by the microprocessor) change in the motor current MC during drill bit penetration (e.g., the second stage 301*b* and/or the third stage 301*c*). In one embodiment, the drill bit cutting face is curved, radiused, or otherwise shaped differently than a linear angle to accentuate the motor current MC rise by increasing the amplitude of the rise or of a time derivative. In another embodiment, the drill bit includes a step or gradient in cutting edge sharpness from point to edge which accentuates the motor current MC rise. In one embodiment, the drill bit has a low point angle (i.e., a flatter tip), such as the cutting tip 214 in FIGS. 2A-2C, configured to reduce or minimize the time between the initial penetration in the second stage 301*b* and the final penetration in the third stage 301*c*. The low point angle is expected to provide a maximum time derivative of current to compare to a threshold, which can lead to a rise/acceleration in the current in the third stage 301*c* that can be identified to detect when the drill bit has penetrated through the skull. In some embodiments, use of the first-time derivative of current dI/dt instead of the current I can be expected to improve autostop repeatability for an increased variety of skull thicknesses, hardnesses, brittlenesses, and other mechanical parameters.

In other embodiments, motor autostop or bit retraction is triggered not by crossing a single threshold in a parameter such as motor current MC, or a single threshold in rate of change of a parameter, but instead by a more complex signal pattern that requires multiple samples of the signal over time. In such embodiments, the autostop trigger occurs when the complete waveshape of the motor current MC includes a specific rise and then fall that occurs over multiple datapoints. As one implementation, a processor within the control electronics compares the waveshape to pre-loaded reference waveshapes and triggers the autostop/autoretraction when the measured waveshape is within a tolerance window of the reference. In some embodiments, the comparison algorithms can be configured to compare the sensor signals in the frequency domain, obtained by performing a Fourier transformation of the measured waveshape.

Figure 5B:
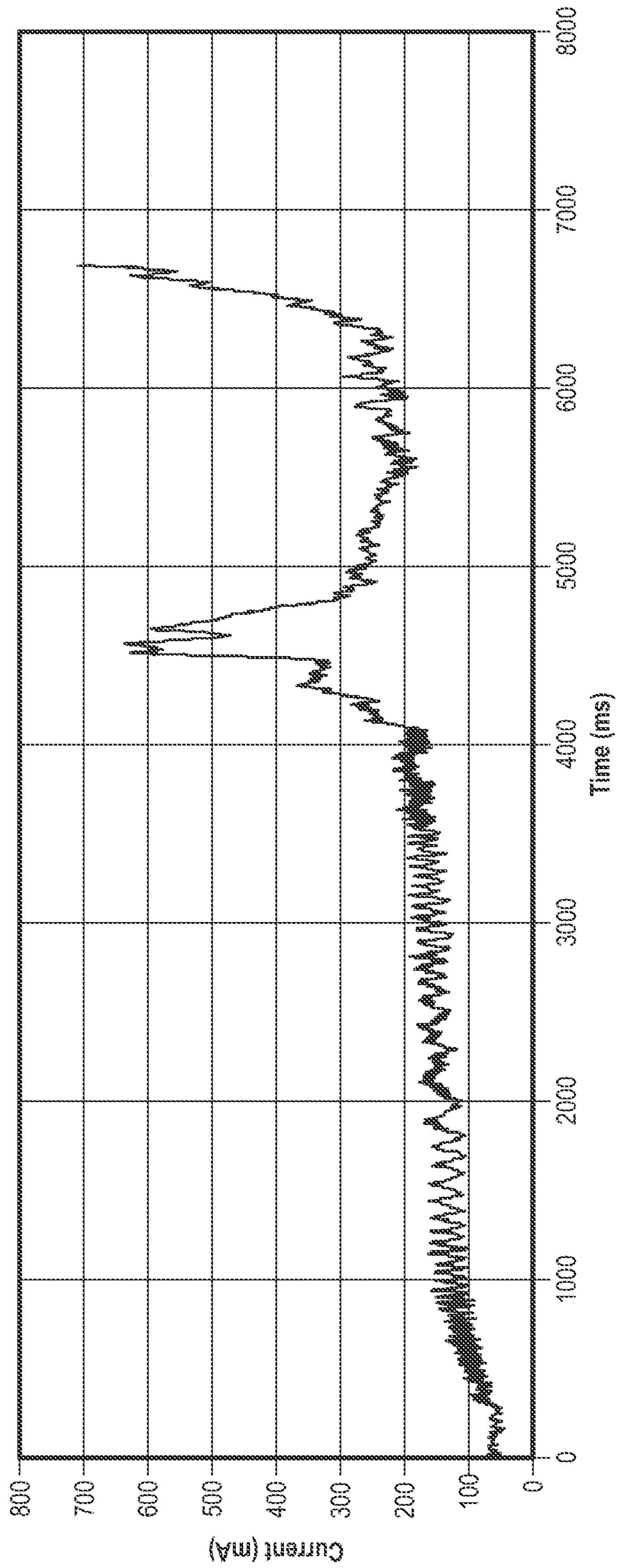
FIG. 5B illustrates a plot of current versus time during a human cadaver trepanation with a constant voltage in accordance with embodiments of the present technology.

FIG. 5B is a plot of current versus time during a trepanation with a constant voltage drill, in accordance with embodiments of the present technology. The human cranium comprises a somewhat hard outer table, a softer middle layer called the 'diploe', and a hard inner table. In one embodiment, the system detects a current spike that occurs as the drill tip penetrates the soft middle layer. In the illustrated embodiment, for example, the current spike at about 4500 ms corresponds to penetration of the soft diploe layer inside the cranium. The system may use this spike as a precondition for identification of the initial penetration point in the second stage 301*b* or the final penetration point in the third stage 301*c* (FIG. 2A). Initial spike detection may also change the drill behavior, for example, by slowing the motor speed, slowing the feed rate (in embodiments with automatic feed rate control), or signaling the user that middle layer (diploe) penetration has occurred. In other embodiments, the system may use a parameter's profile, such as the plot of current versus time of FIG. 5B, to determine the thickness of the outer table and/or the diploe and can additionally use these determined thicknesses to estimate the thickness of the inner table. The estimated inner table thickness, combined with the measured or calculated feed rate, may be fed into an algorithm to provide a further determinant of skull penetration or near-penetration, such as a time-to-penetration or a distance-to-penetration. The inner table thickness estimate may be obtained using at least one of the following: (i) a comparison of the measured and/or inferred outer table and/or diploe thickness against correlated values from a pre-existing reference dataset; or (ii) from a formula and/or lookup table derived from a reference dataset.

In some embodiments, the drill system may use artificial intelligence (AI) and/or machine learning (ML) processes to determine one or more autostop thresholds or triggers, and/or to grow or train the reference dataset. In at least some embodiments, for example, the drill system can record one or more of the parameters described herein (e.g., current draw, time, etc.) and use the one or more parameters to predict when to deactivate the drill motor and/or retract the drill bit. In such embodiments the drill can measure the sensed parameter(s) and, based on the real time sensing of the sensed parameter(s), determine one or more thresholds or triggers for deactivating the drill motor. This can include any of the thresholds (e.g., values, ranges, rates of change, waveforms, profiles, etc.) described previously. The AI and/or ML processes can operate natively on the drill system, and/or via a wireless, cloud-based, or any other suitable communication connection with a remote processing system or server, as described in greater detail below and with reference to FIGS. 14 and 15. If the drill is multi-use or re-useable, the drill may record one or more of the cranial layer thicknesses from each trepanation it performs and store them internally in the reference dataset. If the drill is single use or not re-useable, it may be pre-programmed with the layer thickness correlation data from the reference dataset or may be configured to download (via a wired or wireless connection) the latest reference dataset from a remote database prior to use. The drill, whether single-use or multi-use, may also be configured to upload its layer thickness data to the remote reference dataset after trepanation and prior to disposal, via a wireless connection, a hard storage transfer, a wired connection, or any other suitable connection or transfer process known to those of skill in the art. The correlation reference data may be sorted by patient age, gender, medical status, or any other relevant parameters. The reference data may be limited to past thickness data from the same patient, or may be related to fluoroscopic, MRI, PET or other imaging data from the patient or patients of a similar phenotype.

The embodiments discussed previously and with reference to FIGS. 5A and 5B are not intended to be limiting, and in other embodiments one or more of the drill parameters and/or aspects of the drill system can be altered or otherwise adjusted (e.g., optimized) to produce a repeatable, recognizable signal for the autostop mechanism. FIGS. 6A-13 and the associated descriptions provide details regarding several such other embodiments; however, still other changes that occur to drill parameters between initial penetration point in the second stage 301*b* and final penetration point in the third stage 301*c* and not discussed herein may nevertheless be apparent to those skilled in the art, as will methods of tracking them and methods of shaping them for easier sensing and threshold detection by modification of mechanical drill bit parameters.

Figure 6A:
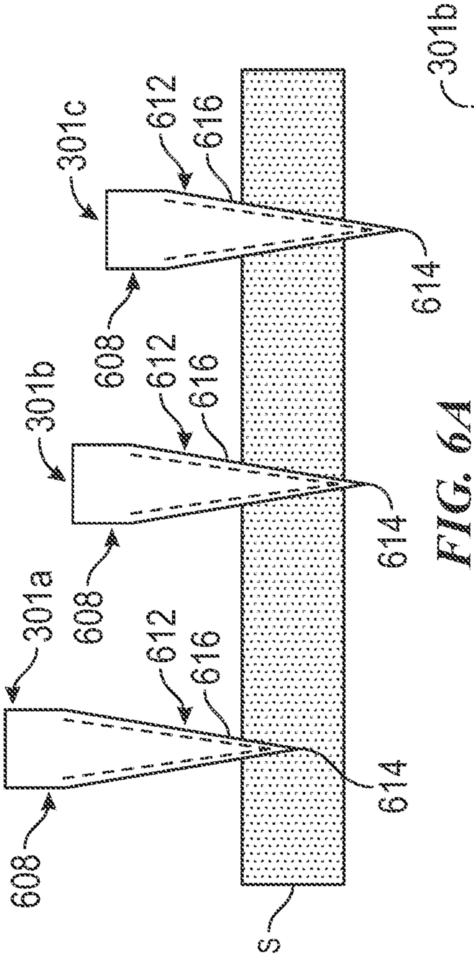
FIG. 6A is a side view of a drill bit having an elongate cutting surface in accordance with embodiments of the present technology.

FIG. 6A is a schematic illustration of a drill bit 608 at various stages of a drilling process, in accordance with embodiments of the present technology. In some embodiments, the sidewall 616 can include a longitudinal taper configured to comprise all or substantially cutting surfaces 612 of the drill bit 608, such that a tip 614 of the drill bit 608 is expected to perform comparatively little to none of the drilling work. In at least some embodiments, for example, the sidewall 616 can comprise at least 60%, 70%, 80%, 90%, 95%, or 99% of the cutting surfaces 612 of the drill bit 608. It is expected that changing the geometry cutting surfaces 612 of the drill bit 608 can change the response of one or more of the parameters described previously and with reference to FIGS. 5A and 5B. In the illustrated embodiment, for example, the elongate cutting sidewall 616 is configured such that at least a portion of the elongate cutting surface remains engaged with the skull throughout the drilling process. Additionally, due to the minimal involvement of the cutting tip 614 in the drilling process, the initial penetration in the second stage 301*b* is not expected to be associated with a substantial or pronounced change in the motor current MC and/or resistance to torque RTT.

Figure 6B:
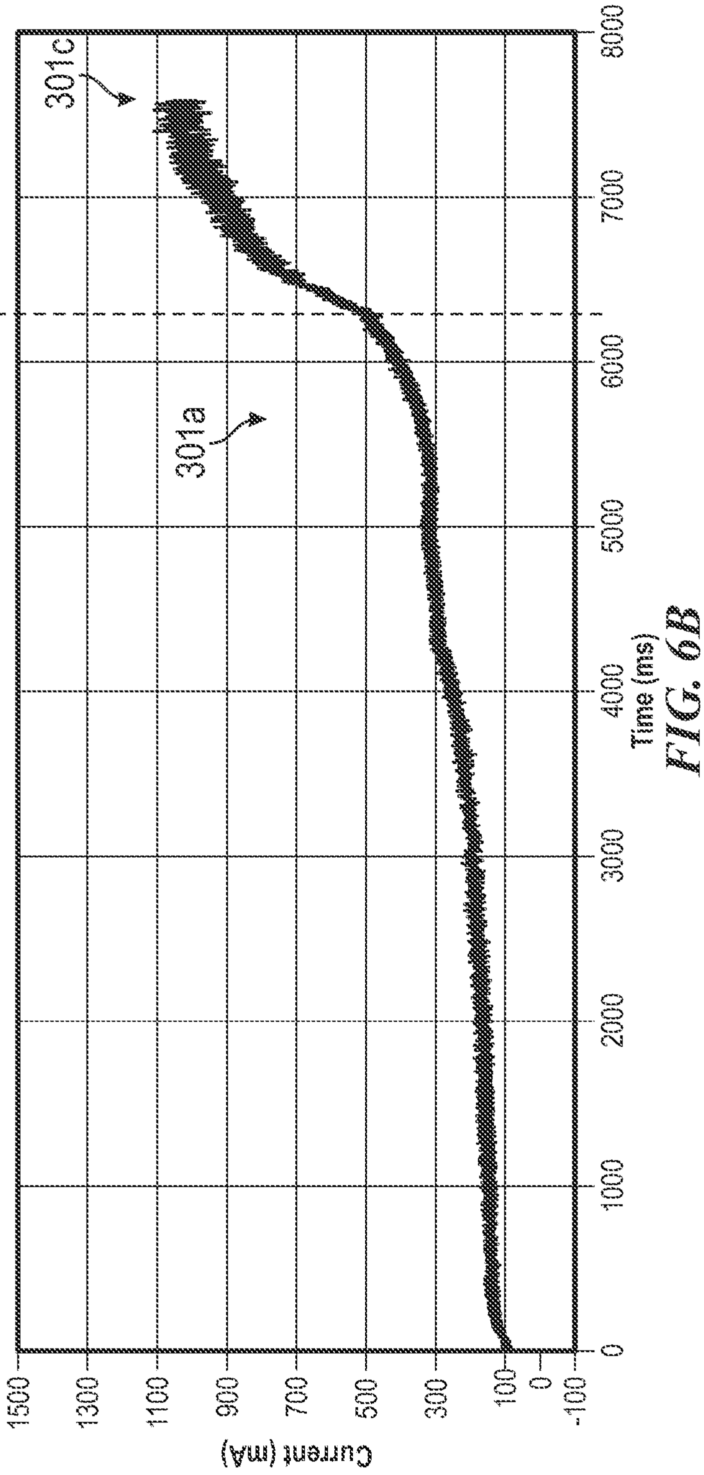
FIG. 6B is a plot of current versus time during a trepanation with a constant voltage drill and the drill bit of FIG. 3A in accordance with embodiments of the present technology.

FIG. 6B illustrates a plot of current versus time during a trepanation with a constant voltage drill and the drill bit 608 of FIG. 6A, in accordance with embodiments of the present technology. As described previously and with reference to FIG. 6A, the shape and/or dimensions of the drill bit can be varied to alter one or more of the parameters. For example, compared to the drill bit 108 associated with FIGS. 3A-4C and/or the drill bit 508 associated with FIGS. 5A and 5B, the different cutting geometry of the drill bit 608 can produce a correspondingly different current draw plot. For example, as illustrated in FIG. 6B, once the skull is initially penetrated in the second stage 301*b*, the current draw remains in a "spiked" or elevated state, due at least in part to the continued contact between the sidewall 616 and the skull S. Accordingly, as described in greater detail previously and with reference to FIGS. 5A and 5B, the drill system compensates by increasing the work input in the rotational direction by the motor. With motor voltage held constant by the system electronics, the increase in work input per motor rotation manifests as an increase in input current, and continues to increase so long as the drill remains in use. The increased current draw can be used as a parameter to indicate a threshold or trigger for automatically stopping the drill motor, such as when the current reaches a threshold or trigger value (e.g., a "high current" threshold value). Accordingly, the size, shape, and/or other dimensions of the drill bit can be varied (e.g., optimized) to produce a desired current draw profile to further improve the repeatability and recognizability of the current draw profile for use with an autostop mechanism.

Figure 7:
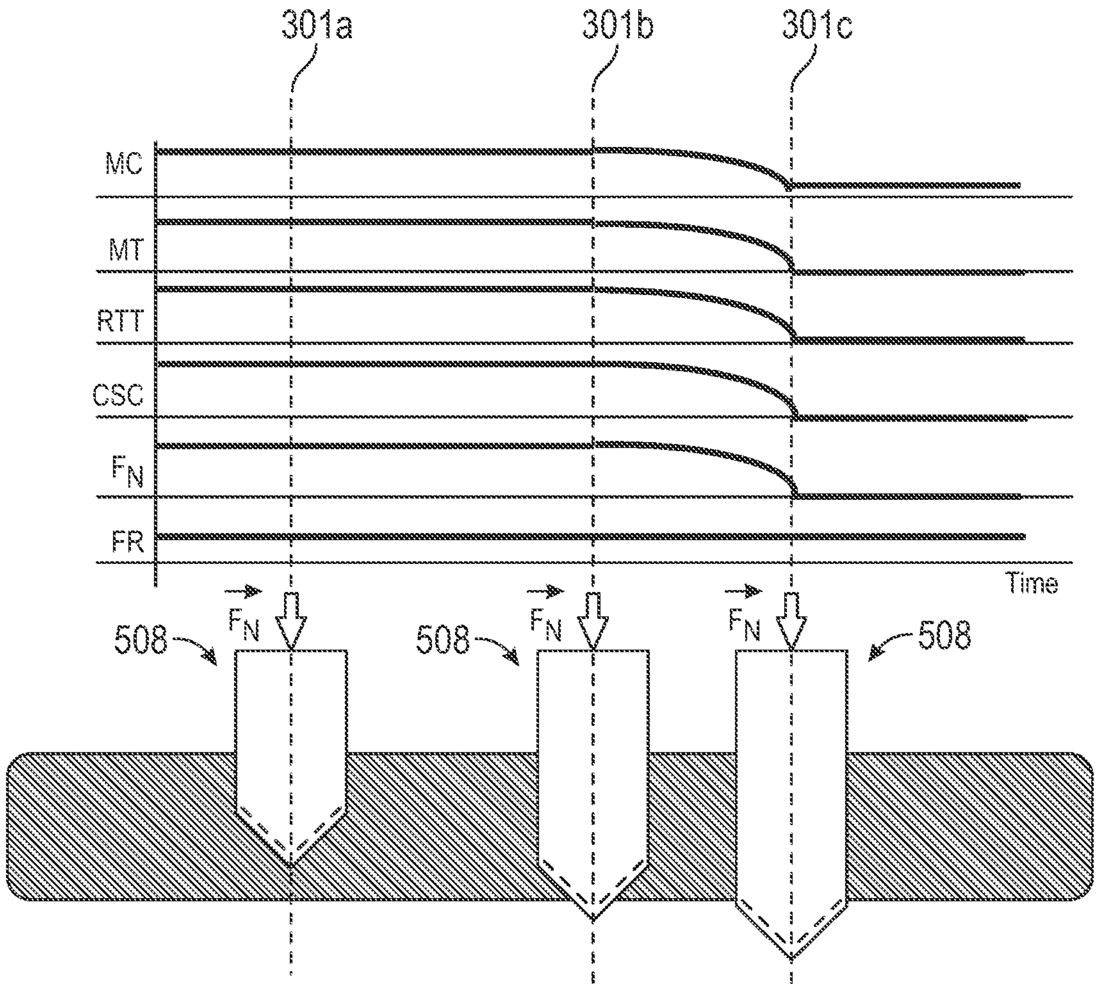
FIG. 7 illustrates transient behavior of the drill parameters of FIG. 2A before, during, and after skull penetration with Normal Force varied to achieve a constant Feed Rate in accordance with embodiments of the present technology.

FIG. 7 illustrates various drill parameters before, during, and after skull penetration, in accordance with embodiments of the present technology. The inventors performed another investigation, generally similar to the investigation represented in FIGS. 5A and 5B, but where the feed rate FR was maintained constant and the normal force $F_N$ was varied. As seen in FIG. 7, the shape of the resultant curves between initial and final penetrations in the second and third stages 301*b*, 301*c* differ from those in the constant normal force $F_N$ case (FIG. 5A). In some embodiments, the feed rate FR is held constant and autostop is triggered by comparing the motor current MC to a low current threshold, such that autostop can be triggered when the motor current MC approaches, reaches, or is within a threshold of the low current threshold. Note that other embodiments also maintain constant feed rate FR as in FIG. 7, or constant normal force $F_N$ as in FIGS. 5A and 5B, by sensing these parameters, and vary the motor current MC or the motor voltage in the alternative. In at least some embodiments, the motor speed and/or the torque MT may be held constant, which can lead to a different repeatable set of parameters that can be used to trigger an autostop mechanism. Although the drill bit 508 illustrated in FIG. 5 is the same as the drill bit 508 in FIGS. 5A and 5B, in other embodiments the drill bit shape can be selected or varied to further enhance (e.g., optimize) one or more of the parameters, so as to attain a strong and repeatable signal for sensing. In at least some embodiments, for example, the conditions of FIG. 7 (varied Normal Force, constant Feed Rate) can be used with the elongate drill bit described previously and with reference to FIGS. 6A and 6B, the drill bit 108 of FIGS. 1-3C, or another suitable drill bit.

Figure 8:
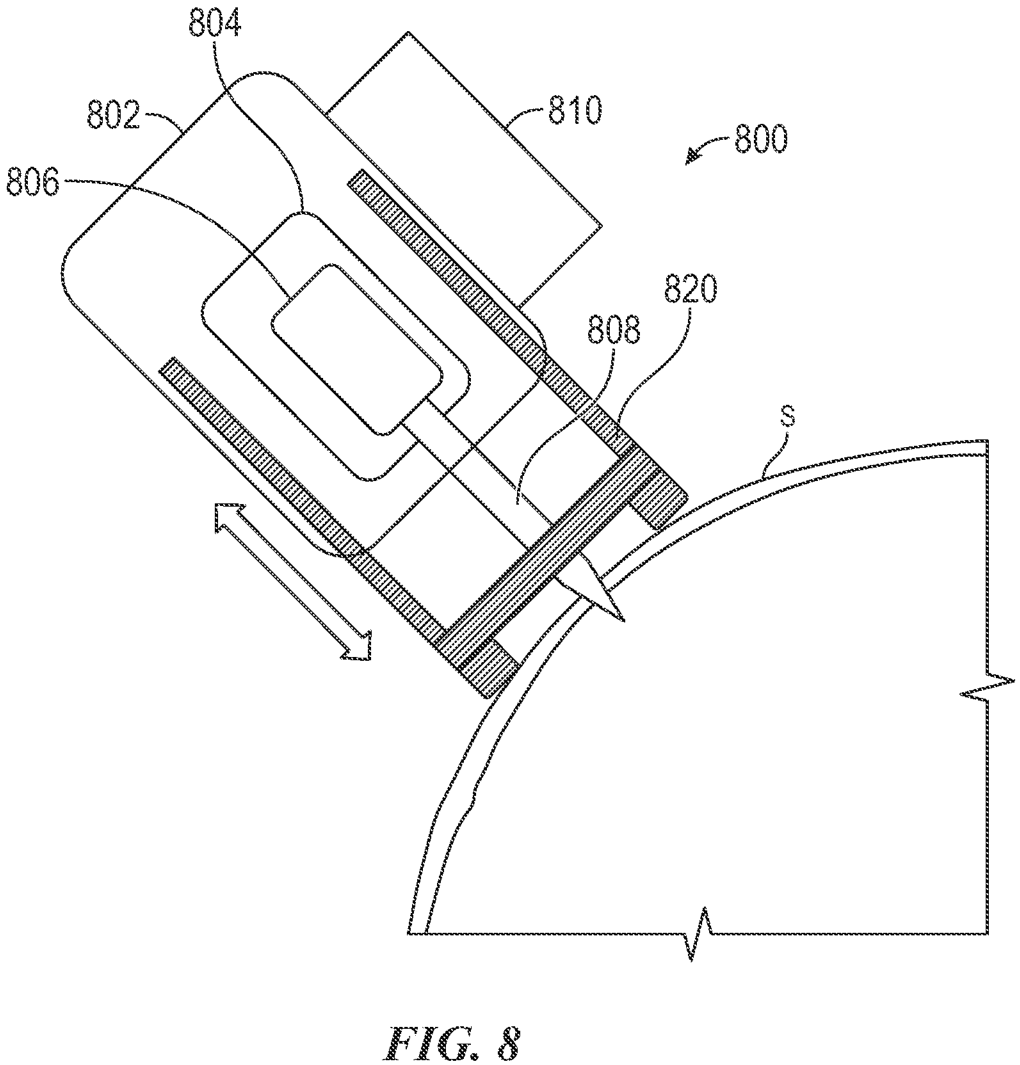
FIG. 8 is a schematic illustration of a motorized cranial drilling system with a drill guide in accordance with embodiments of the present technology.

FIG. 8 is a schematic illustration of a motorized cranial drill 800 ("drill 800") in accordance with embodiments of the present technology. The drill 800 of FIG. 8 can include at least some features that are generally similar or identical in structure and/or function to drill 100 of FIG. 1, but can additionally include a drill guide component 820 ("drill guide 820"). The drill guide 820 can include, for example, the Ghajar Ventriculostomy Kit marketed by Integra Life Sciences, Princeton, NJ, or any other suitable drill guide. In some embodiments, the drill guide 820 includes a mechanical tripod with a guide hole that the operator holds with one hand while holding the drill 100 with the other hand. According to an embodiment, the guide 820 is attached to the patient's head with a strap or mechanical fixture clamped to an operating table. In other embodiments, the guide 820 can be at least partially attached to the patient's head using an adhesive. The drill guide 820 can be configured to keep the drill 800 aligned or positioned relative to a drilling target, and/or to maintain the drill 800 (e.g., the drill bit axis) in a perpendicular orientation relative to the skull S surface. In the illustrated embodiment, the guide 820 can be operably coupled to the housing 802 with a geared, rack-and-pinion, bearing, tooth-and-spring, spring, simple sliding interference fit, or any other suitable coupling. In operation, the guide 820 can be configured to remain stationary relative to the patient's head, such as while the housing 802 moves to, toward, and/or away from the patient's head along the drill axis. The attachment between the guide 820 and the housing 802 can be configured to provide friction to allow increased normal force $F_N$ to be exerted on the housing 802 and/or inhibit or prevent the guide 820 from moving laterally. The electronics 804 can sense the location of the (static) guide 820 relative to the (moving) housing 802 using a system of optical sensors/reflectors or electrical contacts along the guide 820, or any other suitable linear translation sensing methods known in the art. This location sensing allows the electronics 804 and/or the sensing elements 810 to measure the feed rate FR. Strain gages between the guide 820 and housing 802 can allow direct measurement of the normal force $F_N$. Direct measurement of these and other parameters allows algorithms to be developed that exploit the relationships described previously and with reference to FIGS. 4A-4C, 5A, 5B, and 7, so as to identify a parametric signature that indicates that the drill bit is at or near final penetration in the third stage 301*c* and/or initial/partial penetration in the second stage 301*b*.

Figure 9:
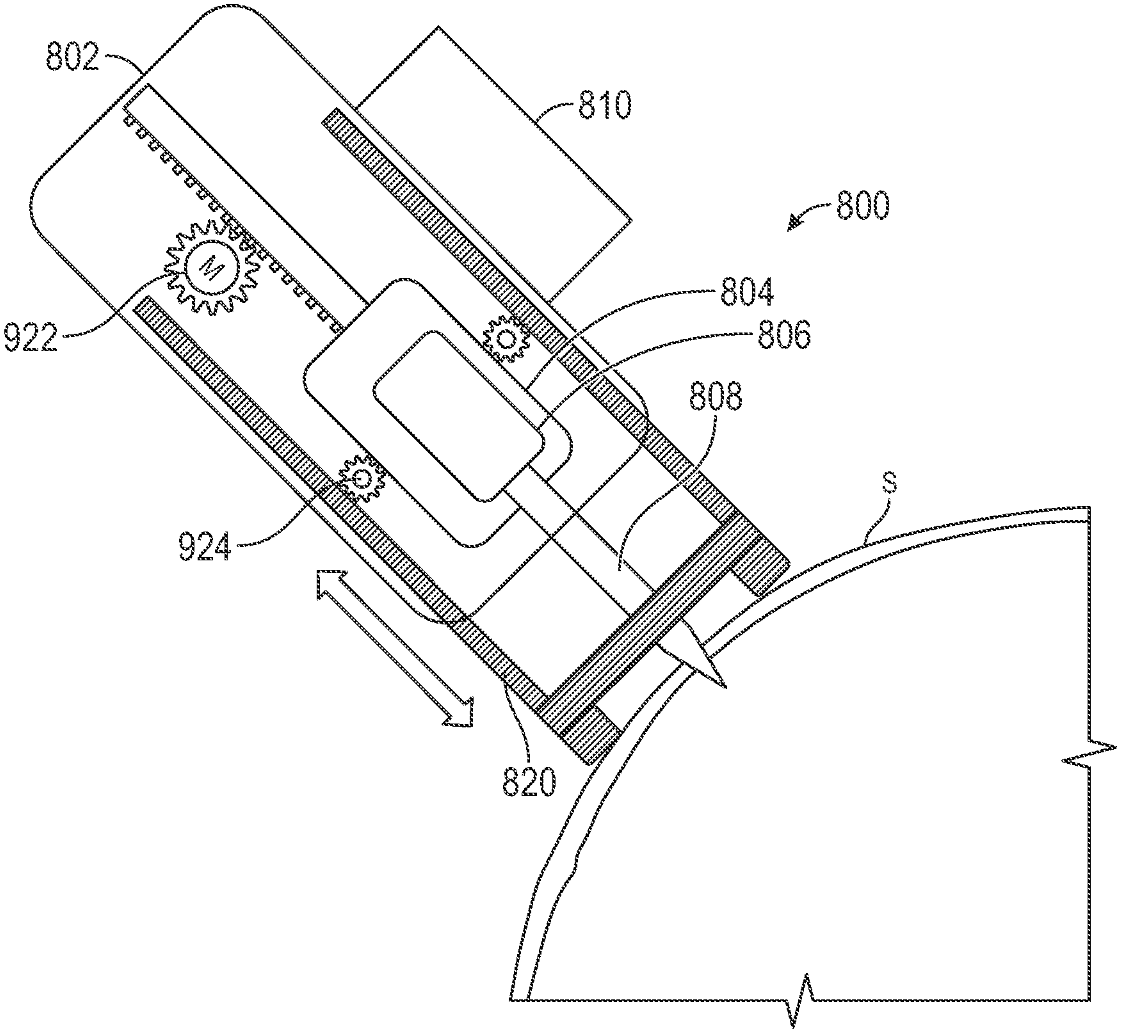
FIG. 9 is a schematic illustration of a motorized cranial drilling system with a drill guide and linear actuation mechanism in accordance with embodiments of the present technology.

FIG. 9 is a schematic illustration of another configuration of the drill 800, in accordance with embodiments of the present technology. In the illustrated embodiment, the drill 800 additionally includes a second motor 922 (e.g., a rotary or linear internal motor) operably coupled to the drill bit 808 and/or the drill bit motor 806 and configured to drive translational of the drill bit 808 and/or the motor 806, e.g., along the drill axis. Additionally, or alternatively, the linear motor 922 can drive one or more gears 924 or other coupling system(s) configured to translate the housing 802 relative to the guide 820. The drill operator can set a desired constant force (e.g., the normal force $F_N$ of FIGS. 5A and 5B) or a constant feed rate (e.g., the feed rate FR of FIG. 4), and can hold the guide 820 in place by hand or using a strap or fixture while the drill 800 moves automatically relative to the guide 820. In such embodiments, the normal force $F_N$ or the feed rate FR can be kept constant, providing the characteristic signals described previously and with reference to FIGS. 5A, 5B, and 7, respectively. Accordingly, the drill system 800 can be configured to automatically stop the drill motor 806 and/or retract the drill bit 808 via the linear motor 922 based at least in part on one or more of the parameters described previously and with reference to FIG. 4A-5B or 7, respectively. In other embodiments, other algorithms can be programmed into the control electronics to provide variable force or feed rate FR according to preset values or in response to real-time measured parameters including, for example, the algorithms described in greater detail below. In addition to controlling linear translation, the actuator depicted can also be used for bit retraction at the point of final penetration in the third stage 301*c* or partial penetration in the second stage 301*b*.

Figure 10:
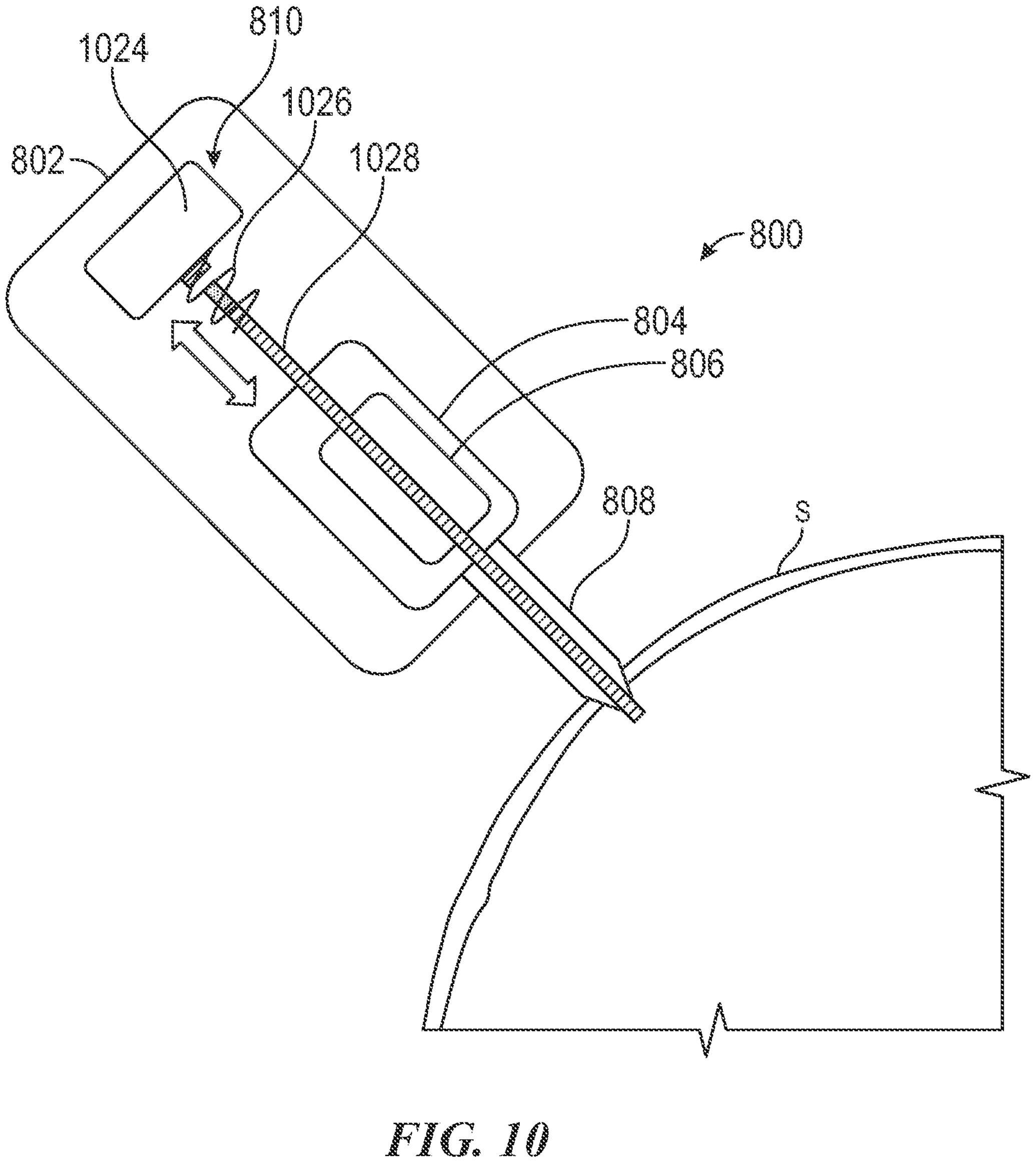
FIGS. 10-13 are schematic illustrations of additional cranial drilling systems, each configured in accordance with embodiments of the present technology.

FIG. 10 is a schematic illustration of another configuration of the drilling system 800 in accordance with embodiments of the present technology. In the illustrated embodiment, the motor 804, the drill bit 808, and the electronics 804 can be carried by the housing 802, and the sensing elements 810 can include a contact switch 1024, a spring 1026, and a rod 1028. The rod 1028 configured to translate linearly along its longitudinal axis. Prior to penetrating the skull bone, the normal force applied to the drill bit 808 can compress the spring 1026 such that the rod 1028 and the contact switch 1024 (e.g., a proximity sensor, a strain gauge, and/or any other suitable sensing element 810) can contact each other. When the drill bit 808 at least partially penetrates the skull S, the normal force can decrease such that the spring 1026 can expand and apply a force to the rod 828 in a direction away from the contact switch 1024, which, in turn, can trigger an indicator of skull penetration (e.g., moving the rod 1028 away from a proximity sensor, increasing a strain reading between the rod 1028 and a strain gauge, etc.). In various embodiments, the rod 1028 may be electrically connected to a fixed contact or push against a membrane switch when the spring 1026 is compressed but may break contact when the spring 1026 relaxes upon skull penetration, triggering the electronic indicator.

Figure 11:
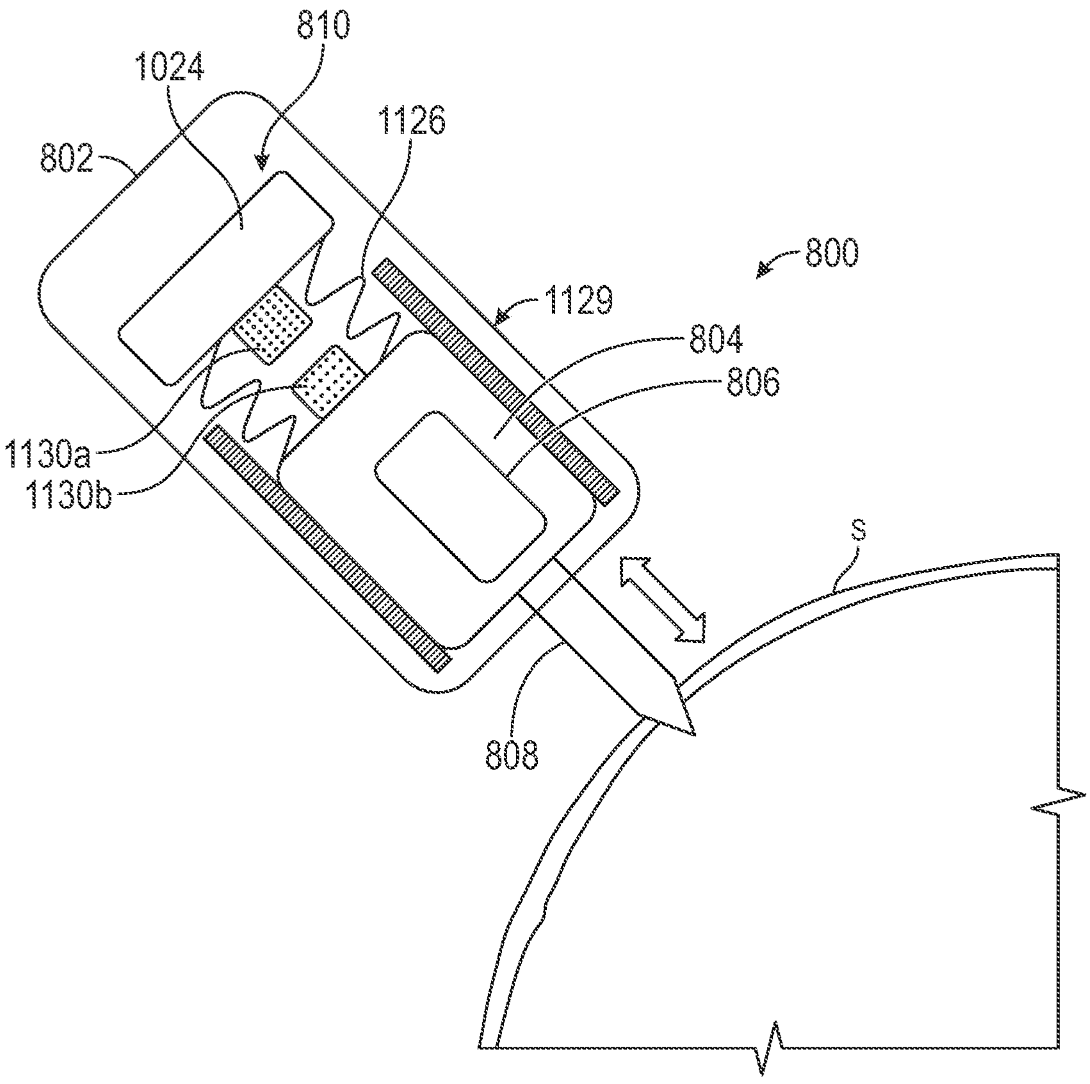

FIG. 11 is a schematic illustration of another configuration of the drilling system, in accordance with embodiments of the present technology. In the illustrated embodiment, the motor 806, the bit 808, and the electronics 804 can be connected together to form an assembly that can be movably coupled to an interior of the housing 802, e.g., such that the assembly can translate relative to the housing 802 (e.g., translate linearly relative to a longitudinal axis of the housing 802). The drill 800 can further include a contact switch

1024 (e.g., a proximity sensor, a strain gauge, and/or any other suitable sensing element(s) 810) that can have a fixed position relative to the housing 802. In some embodiments, the contact switch 1024 includes a first contact 1130*a* and the assembly can include a second contact 1130*b*, and the contact switch 1124 and the assembly can be coupled by one or more springs 1126 (e.g., compression springs). In other embodiments, the drill system 800 can include more than two or fewer than two contacts 1130*a-b*. As described above, prior to penetrating the skull bone, the normal force applied to the drill bit 808 can compress the spring(s) 1126, which causes the first and second contacts 1130*a-b* to move toward and/or contact one another. When bit 808 penetrates skull S, the spring(s) 1126 can expand in a direction away from the contact switch 1124 and drive the assembly away from the contact switch 1024 to trigger an indicator of skull penetration (e.g., by moving the second contact 1130*b* away from and/or out of contact with the first contact 1130*a*).

Figure 12:
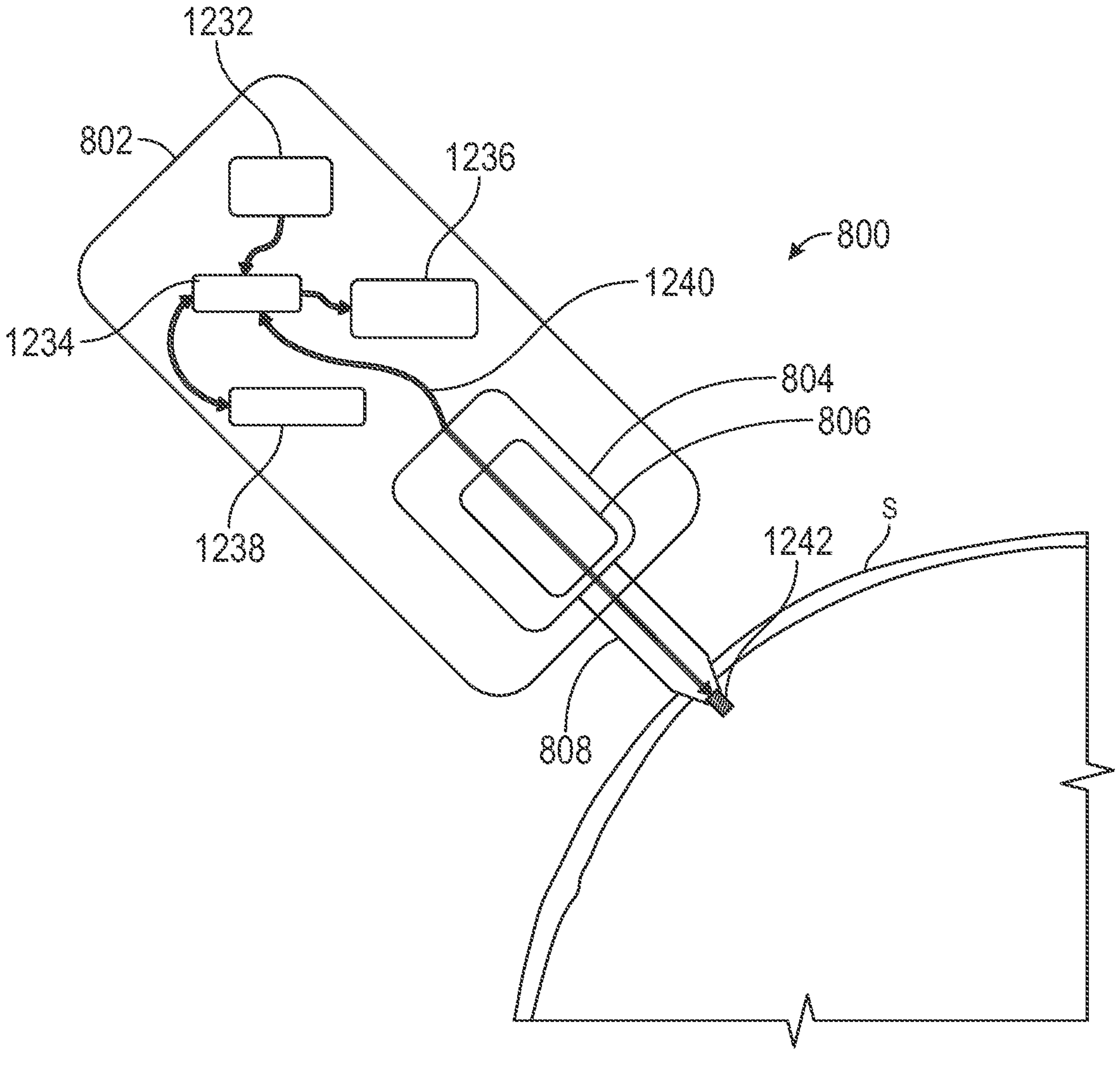
Figure 13:
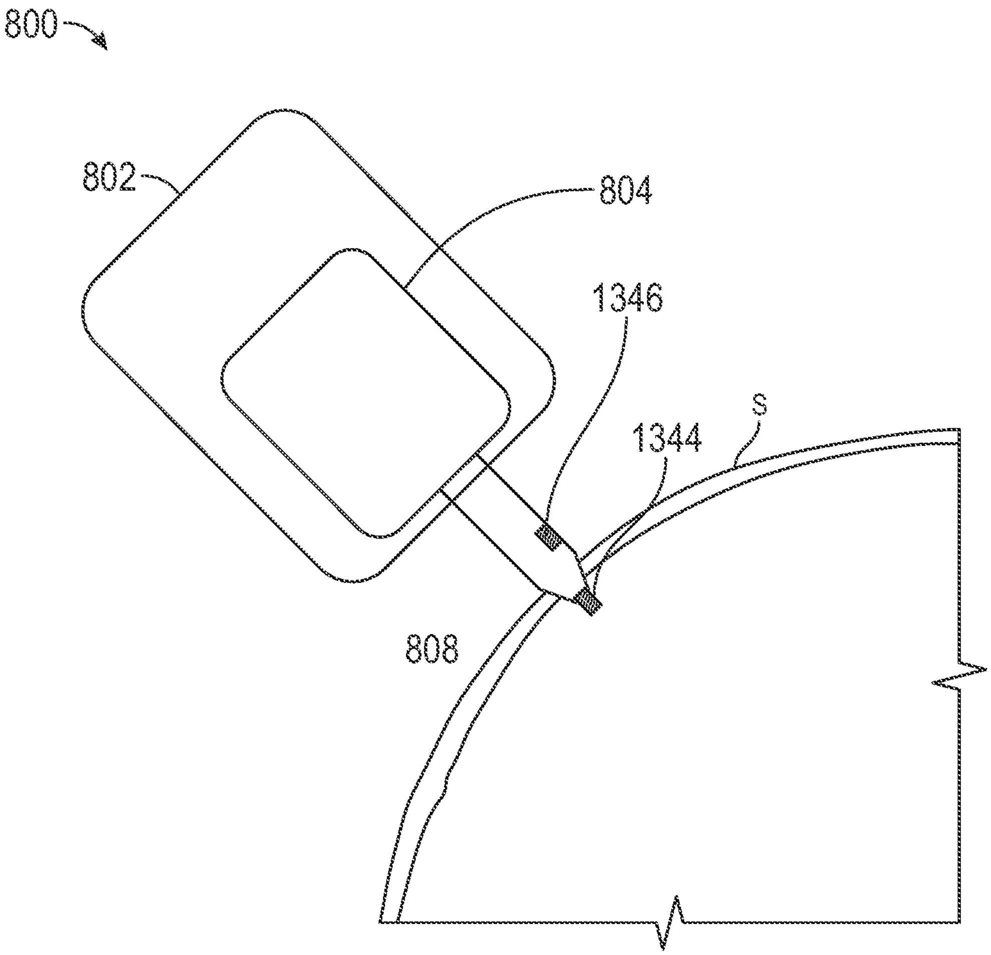

In still further embodiments, such as the embodiment illustrated in FIG. 12, the drill 800 may include an optical system that projects light energy from a laser or other optical source 1232 through a hole or focusing element 1242 in the distal tip of the bit 808, and measures the amplitude, phase, or wavelength content of backscattered light. In the illustrated embodiment, for example, the optical source 1232 includes a light energy source (e.g., a laser source) and the focusing element 1232 includes a micro lens, such as any suitable optical lens or light-focusing element. The light energy source 1232 can be coupled to the micro lens 1242 by one or more optical fibers 1240, or any other suitable waveguide connecting element, such that light from the light energy source 1232 can project through the micro lens 1242 and toward the skull S and/or cranial tissue. At least a portion of the projected light can be incident on the skull S be and backscattered, reflected, and/or otherwise redirected toward the micro lens 1242. The micro lens 1242 can be configured to capture backscattered light. The backscattered light can be analyzed using, for example, a phase detector 1236, a reference light source 1238, and/or any other suitable analysis process and/or component. If one of these properties of the backscattered/incident light changes when the reflection surface changes from one skull layer to another, or from skull to meninges, the control algorithm may use this to trigger a change in drill actuation, such as autostop, autoretraction or motor torque. In various embodiments, technologies such as optical coherence tomography (OCT), optical coherence reflectometry (OCR), or optical spectroscopy may be used to detect changes in one or more tissue properties, such as tissue birefringence, tissue density, or tissue composition. Such technologies can detect changes in the properties of cranial tissue(s) just below (e.g., proximate) the tip of the drill bit 808 and/or at depths of one or more millimeters into the tissue. Such detected changes in tissue properties can be used to provide a stop (e.g., autostop), slowdown, and/or other suitable user alert signal before the drill bit 808 tip penetrates the skull. Embodiments of these and other drilling systems can house all optical components inside the drill housing 802, or can house only a portion of the optical components inside the drill housing 802, such as the optical fiber(s) 1240 and lens 1242 in the drill housing 802. In some embodiments, the drill 800 can be connected to a non-disposable external device (not shown) with a fiberoptic cable or similar waveguide, and the external device can contain one or more laser sources, optical detectors, splitters, combiners, circulators, filters, phase detectors, lenses, mirrors, polarizers, waveplates, reference waveguides, gratings, and/or any other suitable elements of the optical system. In these and other embodiments, the optical system may also be configured to perform an amplitude scan (A-Scan) and/or brightness scan (B-Scan) to determine a remaining distance to skull penetration. In still further embodiments, the optical system can include planar optics, silicon optical benches, rigid waveguides, acousto-optics, electro-optics, and/or free space optics.

In still other embodiments, the drill bit 808 tip is provided with an ultrasonic transducer that resonates to impose ultrasonic energy into the skull. In the embodiment illustrated in FIG. 13, for example, the drill 800 may include one or more acoustic drilling components 1344 (e.g., an ultrasonic actuator, ultrasonic drill, ultrasonically assisted drilling, an ultrasonic percussion drill) configured to vibrate at least a portion of the drill bit 808 (e.g., the drill bit 808 tip) to penetrate through the skull S. In such embodiments, the electronics 804 can include one or more acoustic drilling drive elements operably coupled to, and/or configured to control operation of, the acoustic drilling elements 1344. In these and other embodiments, the drill 800 can also include a lumen or shunt (not shown) operably associated with the drill bit 808 and configured to remove the slurry generated by drilling. In these and other embodiments, the drill 800 can include one or more acoustic sensors 1346 (e.g., acoustic detectors) positioned on or proximate the drill bit 808 tip, and/or any other suitable position, such that the acoustic sensors 1346 can receive reflected waves generated in response to the acoustic drilling elements 1344. The drill system 800 can be configured to determine whether the drill bit 808 tip is near penetration based at least partially on a characteristic acoustic signature detected by the acoustic sensor(s) 1346. The characteristic acoustic signature can include an ultrasonographic amplitude scan (A-Scan), a brightness scan (B-Scan), and/or any other suitable characteristic acoustic signature. As with the optical embodiments, ultrasonic embodiments could place all components in the drill housing 802, or can distribute elements of the ultrasonic sensing system between the drill 800 and an external unit (not shown). In these and other embodiments, the drilling system 800 can include one or more rigid and/or acoustically conductive (e.g., resonant) components positioned to communicate ultrasonic energy between the drilling system 800 and the skull S, for example, to obtain the amplitude scan and/or any other suitable acoustic information.

Various embodiments may include one or more algorithms configured to detect when the drill bit has initially and/or fully penetrated the skull S and automatically stop the drill bit. For example, the algorithm can include holding either feed rate FR or the normal force $F_n$ constant and comparing the level, rate of change, area under curve, rise time, fall time, or general shape of the motor current MC change (e.g., acceleration) just prior to moment of partial penetration in the second stage 301*b* and/or full penetration in the third stage 301*c*. In these and other embodiments, the algorithm can include combining the above with an 'enable' signal, the enable signal asserted by detection of current rise and fall as the drill passes through the diploe layer described previously with reference to FIG. 5B, or other suitable skull layers. In these and other embodiments, the algorithm can include placing a torque sensor or a speed sensor on the rotating motor shaft and triggering autostop when the motor torque, motor current, or motor speed rise (FIGS. 5A and 5B) or fall (FIG. 7). For the conditions described with reference to at least FIGS. 5A and 5B (e.g., constant normal force $F_N$) case, the algorithm can include triggering autostop when feed rate rises rapidly, on its own or in combination with motor current rise. For the conditions described with reference to at least FIG. 7 (e.g., constant feed rate FR) case, the algorithm can include triggering autostop when the normal force $F_N$ decreases toward and/or to zero, on its own or in combination with motor current MC drop-off. In these and other embodiments, the algorithm can include placing a force sensor or strain gage on the linear shaft of FIG. 9 or on the linear motor 922 or on the gears 924, or measuring current in the linear motor 922, and using this to determine normal force $F_N$ for either detecting normal force drop-off (FIG. 7) or for holding normal force steady (FIGS. 5A and 5B). In these and other embodiments, the algorithm can include detecting initial penetration in the second stage 301*b* by a spring-rod switch, a contact switch, an acoustic drilling device and/or acoustic sensing system, an ultrasonic drilling device and/or ultrasonic sensing system, and/or an optical sensing system. In these and other embodiments, the algorithm can include counting current acceleration, such as via an analog-to-digital converter, and causing the drill bit to stop after the count reaches a specified value. In at least some embodiments, for example, each count can correspond to an about 0.04 $mA/s^2$ current acceleration, and the drill can be configured to stop the drill bit once the count reaches 50, corresponding to an about 2.5 $mA/s^2$ acceleration in current. In other embodiments, the specified value can correspond to a current acceleration between about 0.01 $mA/s^2$ and about 5 $mA/s^2$, or another suitable current acceleration.

The techniques disclosed herein can be embodied as special-purpose hardware (e.g., circuitry), as programmable circuitry appropriately programmed with software and/or firmware, or as a combination of special-purpose and programmable circuitry. Hence, some embodiments may include a machine-readable medium having stored thereon instructions which may be used to cause a computer, a microprocessor, processor, and/or microcontroller (or other electronic devices) to perform a process. The machine-readable medium may include, but is not limited to, optical disks, compact disc read-only memories (CD-ROMs), magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions.

Figure 14:
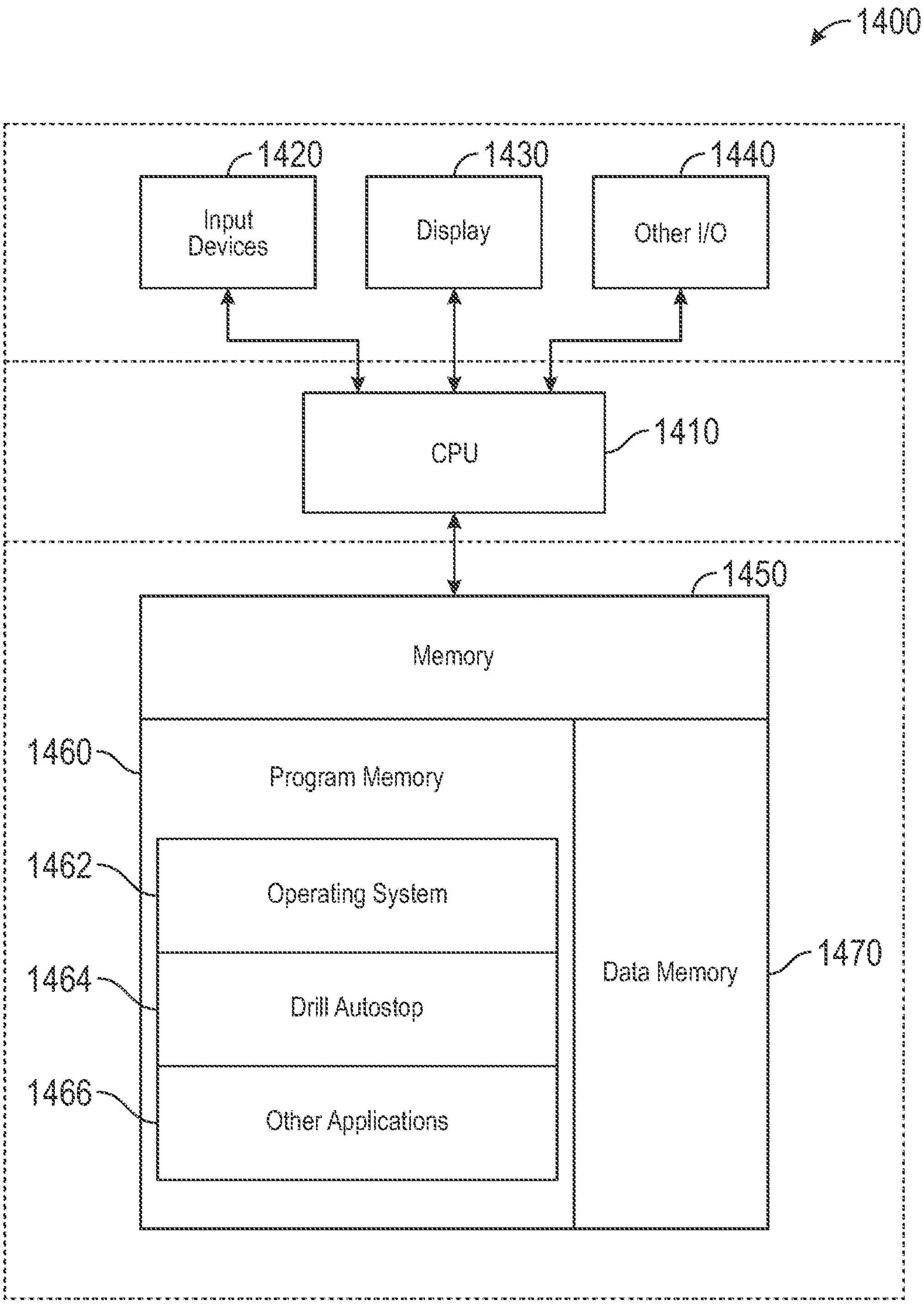
FIG. 14 is a block diagram illustrating an overview of devices on which some embodiments of the present technology can operate.

Several implementations are discussed below in more detail in reference to the figures. FIG. 14 is a block diagram illustrating an overview of devices on which some implementations of the disclosed technology can operate. The devices can comprise hardware components of a system 1400 that determines one or more automatic stop thresholds and/or stops drill bits based at least partially on one or more drilling parameters, for example. Device 1400 can include one or more input devices 1420 that provide input to the CPU (processor) 1410, notifying it of actions. The actions are typically mediated by a hardware controller that interprets the signals received from the input device and communicates the information to the CPU 1410 using a communication protocol. Input devices 1420 include, for example, a mouse, a keyboard, a touchscreen, an infrared sensor, a touchpad, a wearable input device, a camera-or image-based input device, a microphone, or other user input devices.

CPU 1410 can be a single processing unit or multiple processing units in a device or distributed across multiple devices. CPU 1410 can be coupled to other hardware devices, for example, with the use of a bus, such as a PCI bus or SCSI bus. The CPU 1410 can communicate with a hardware controller for devices, such as for a display 1430. Display 1430 can be used to display text and graphics. In some examples, display 1430 provides graphical and textual visual feedback to a user. In some implementations, display 1430 includes the input device as part of the display, such as when the input device is a touchscreen or is equipped with an eye direction monitoring system. In some implementations, the display is separate from the input device. Examples of display devices are: an LCD display screen; an LED display screen; a projected, holographic, or augmented reality display (such as a heads-up display device or a head-mounted device); and so on. Other I/O devices 1440 can also be coupled to the processor, such as a network card, video card, audio card, USB, FireWire or other external device, sensor, camera, printer, speakers, CD-ROM drive, DVD drive, disk drive, or Blu-Ray device.

In some implementations, the device 1400 also includes a communication device capable of communicating wirelessly or wire-based with a network node. The communication device can communicate with another device or a server through a network using, for example, TCP/IP protocols. Device 1400 can utilize the communication device to distribute operations across multiple network devices.

The CPU 1410 can have access to a memory 1450. A memory includes one or more of various hardware devices for volatile and non-volatile storage and can include both read-only and writable memory. For example, a memory can comprise random access memory (RAM), CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. Memory 1450 can include program memory 1460 that stores programs and software, such as an operating system 1462, Drill Autostop 1464 (which may include instructions for carrying out one or more of the methods of automatic drill stopping disclosed herein, including, for example, one or more AI and/or ML systems or processes), and other application programs 1466. Memory 1450 can also include data memory 1470 that can include database information, etc., which can be provided to the program memory 1460 or any element of the device 1400.

Some implementations can be operational with numerous other general purpose or special purpose computing system environments or configurations. Examples of well-known computing systems, environments, and/or configurations that may be suitable for use with the technology include, but are not limited to, personal computers, server computers, handheld or laptop devices, cellular telephones, mobile phones, wearable electronics, gaming consoles, tablet devices, multiprocessor systems, microprocessor-based systems, set-top boxes, programmable consumer electronics, network PCs, minicomputers, mainframe computers, distributed computing environments that include any of the above systems or devices, or the like.

Figure 15:
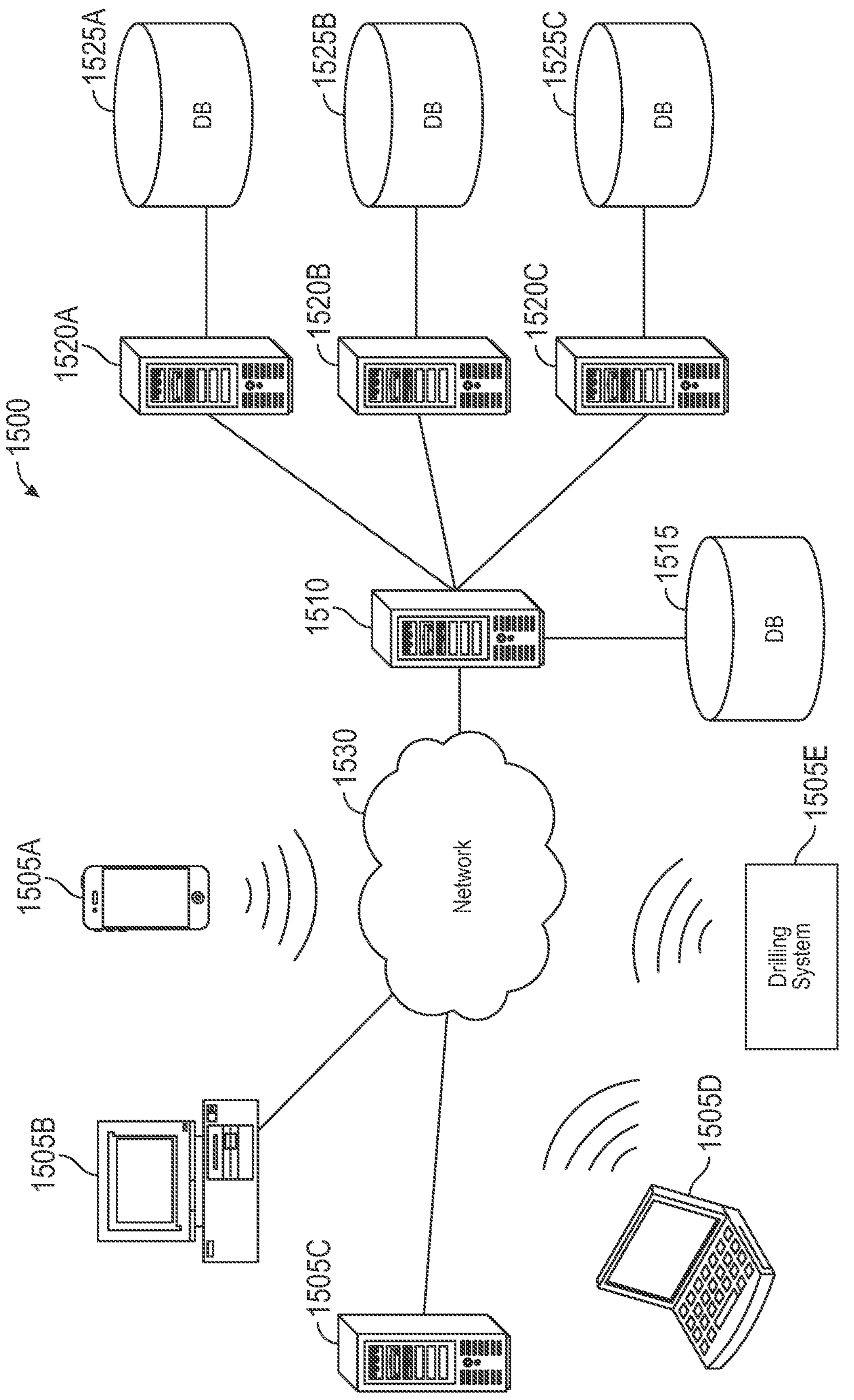
FIG. 15 is a block diagram illustrating an overview of an environment in which some embodiments of the present technology can operate.

FIG. 15 is a block diagram illustrating an overview of an environment 1500 in which some implementations of the disclosed technology can operate. Environment 1500 can include one or more client computing devices 1505A-E, examples of which can include the device 1400. Client computing devices 1505 can operate in a networked environment using logical connections through network 1530 to one or more remote computers, such as a server computing device 1510.

In some implementations, server computing device 1510 can be an edge server that receives client requests and coordinates fulfillment of those requests through other servers, such as servers 1520A-C. Server computing devices 1510 and 1520 can comprise computing systems, such as device 1400. Though each server computing device 1510 and 1520 is displayed logically as a single server, server computing devices can each be a distributed computing environment encompassing multiple computing devices located at the same or at geographically disparate physical locations. In some implementations, each server computing device 1520 corresponds to a group of servers.

Client computing devices 1505 and server computing devices 1510 and 1520 can each act as a server or client to other server/client devices. Server 1510 can connect to a database 1515. Servers 1520A-C can each connect to a corresponding database 1525A-C. As discussed above, each server 1520 can correspond to a group of servers, and each of these servers can share a database or can have their own database. Databases 1515 and 1525 can warehouse (e.g., store) information. Though databases 1515 and 1525 are displayed logically as single units, databases 1515 and 1525 can each be a distributed computing environment encompassing multiple computing devices, can be located within their corresponding server, or can be located at the same or at geographically disparate physical locations.

Network 1530 can be a local area network (LAN) or a wide area network (WAN) but can also be other wired or wireless networks. Network 1530 may be the Internet or some other public or private network. Client computing devices 1505 can be connected to network 1530 through a network interface, such as by wired or wireless communication. While the connections between server 1510 and servers 1520 are shown as separate connections, these connections can be any kind of local, wide area, wired, or wireless network, including network 1530 or a separate public or private network.

Those skilled in the art will appreciate that the components illustrated in FIGS. 14 and 15 described above, and in each of the flow diagrams discussed above, may be altered in a variety of ways. For example, the order of the logic may be rearranged, sub steps may be performed in parallel, illustrated logic may be omitted, other logic may be included, etc. In some implementations, one or more of the components described above can execute one or more of the processes described herein.

EXAMPLES

Several aspects of the present technology are described with reference to the following examples:

1. A surgical drilling device comprising:
   - a drill bit having a cutting surface, wherein at least a portion of the cutting surface is configured to remain in contact with a skull of a patient when in operation;
   - a drill motor operably coupled to the drill bit, wherein the drill motor is configured to generate a parameter when in operation, and wherein the parameter is associated with the cutting surface; and
   - a sensing element configured to detect the parameter,
   - wherein, when the sensing element detects the parameter meets or exceeds a triggering threshold, the drill motor is configured to stop and thereby inhibit rotation of the drill bit.
2. The surgical drilling device of example 1 wherein the parameter includes a second derivative of current drawn by the drill motor when in operation.
3. The surgical drilling device of example 1 or example 2 wherein the cutting surface is configured to cause an increase in the parameter when the drill bit penetrates through the skull.
4. The surgical drilling device of any of examples 1-3 wherein the cutting surface is configured to cause the parameter to meet or exceed the triggering threshold when the drill bit penetrates through the skull.
5. The surgical drilling device of any of examples 1-4 wherein the cutting surface includes a tapered sidewall, wherein the drill bit further includes a cutting tip, wherein the parameter includes an acceleration of current drawn by the drill motor when in operation, and wherein the tapered sidewall is configured to cause the acceleration of current to meet or exceed the triggering threshold at or after penetration of the cutting tip through the skull.
6. The surgical drilling device of any of examples 1-5 wherein the cutting surface includes a sidewall of the drill bit.
7. The surgical drilling device of example 6 wherein at least a portion of the sidewall is configured to maintain contact with the skull after the drill bit has penetrated through the skull.
8. The surgical drilling device of example 6 or example 7 wherein the sidewall is tapered relative to a longitudinal axis of the drill bit.
9. The surgical drilling device of any of examples 6-8 wherein the sidewall is at a five-degree angle relative to a longitudinal axis of the drill bit.
10. The surgical drilling device of any of examples 6-9 wherein the drill bit further includes a cutting tip at a distal end of the drill bit, wherein the sidewall extends proximally from the cutting tip.
11. The surgical drilling device of example 10 wherein the sidewall is angled radially outward and in a proximal direction from the cutting tip.
12. The surgical drilling device of example 10 or example 11 wherein the triggering threshold includes a value of the parameter associated with penetration of the cutting tip through the skull.
13. The surgical drilling device of any of examples 1-12 wherein the drill bit further includes a flute extending in a direction parallel to a longitudinal axis of the drill bit.
14. The surgical drilling device of example 13 wherein the flute has a linear shape.
15. The surgical drilling device of any of examples 1-14 wherein the sensing element includes an analog-to-digital converter.
16. The surgical drilling device of any of examples 1-15 wherein the parameter includes at least one of a drill motor current, a drill motor torque, a drill motor resistance to torque, a drill bit cutting lip contact, a drill bit feed rate, and/or a normal force applied to the drill bit.
17. The surgical drilling device of any of examples 1-16 wherein the parameter is a first parameter and the triggering threshold is a first triggering threshold, and wherein the drill motor is configured to (i) generate a second parameter when in operation and (ii) stop to thereby inhibit rotation of the drill bit when the second parameter meets or exceeds a second triggering threshold.
18. One or more non-transitory computer readable media having instructions stored thereon that, when executed by one or more processors of a drilling system, cause the drilling system to perform operations comprising:

providing power to a drill motor to cause rotation of a drill bit of the drilling system, wherein the drill bit includes a cutting surface, and wherein at least a portion of the cutting surface is configured to contact a skull of a patient when in operation;

determining, via a sensing element of the drilling system, a parameter of the drill motor including at least one of a drill motor current, a drill motor torque, a drill motor resistance to torque, a drill bit cutting lip contact, a drill bit feed rate, and/or a normal force applied to the drill bit, wherein the parameter corresponds to a shape of the cutting surface; and when the parameter meets or exceeds a triggering threshold, causing the drill motor to stop the rotation of the drill bit.

19. The one or more non-transitory computer readable media of example 18 wherein determining the parameter includes determining a second derivative of the drill motor current.

20. The one or more non-transitory computer readable media of example 18 or example 19, the operations further comprising causing, based at least in part on contact between the cutting surface and the skull at or near penetration of the drill bit through the skull, an increase in the parameter when the drill bit penetrates through the skull.

21. The one or more non-transitory computer readable media of any of examples 18-20, the operations further comprising causing, based at least in part on contact between the cutting surface and the skull, the parameter to meet or exceed the triggering threshold when the drill bit penetrates through the skull.

22. The one or more non-transitory computer readable media of any of examples 18-21 wherein the cutting surface includes a tapered sidewall and the drill bit further includes a cutting tip, the operations further comprising causing, based at least in part on contact between the sidewall and the skull, an acceleration of current drawn by the drill motor to meet or exceed the triggering threshold at or after penetration of the cutting tip through the skull.

23. The one or more non-transitory computer readable media of any of examples 18-22 wherein the triggering threshold includes a value of the parameter associated with penetration of the drill bit through the skull, and wherein causing the drill motor to stop the rotation of the drill bit includes causing the drill motor to stop the rotation of the drill bit when the parameter meets or exceeds the value.

24. The one or more non-transitory computer readable media of any of examples 18-23 wherein the parameter is a first parameter and the triggering threshold is a first triggering threshold, and wherein the instructions are further configured to cause the drill motor to stop the rotation of the drill bit when a second parameter of the drill motor meets or exceeds a second triggering threshold.

25. A method of operating a surgical drilling device, comprising:

providing power to a drill motor to cause rotation of a drill bit of the surgical drilling device, wherein the drill bit includes a cutting surface, and wherein at least a portion of the cutting surface is configured to contact a skull of a patient when in operation;

determining, via a sensing element of the surgical drilling device, a parameter of the drill motor, wherein the parameter corresponds to a shape of the cutting surface; and when the parameter meets or exceeds a triggering threshold, causing the drill motor to stop the rotation of the drill bit.

26. The method of example 25 wherein determining the parameter includes determining a second derivative of current drawn by the drill motor when in operation.

27. The method of example 25 or example 26 wherein causing the drill motor to stop includes causing the drill motor to stop based at least in part on an increase in the parameter when the drill bit penetrates through the skull.

28. The surgical drilling device of any of examples 25-27, further comprising causing, based at least in part on contact between the cutting surface and the skull, the parameter to meet or exceed the triggering threshold when the drill bit penetrates through the skull.

29. The method of any of examples 25-28, wherein the cutting surface includes a tapered sidewall and the drill bit further includes a cutting tip, further comprising causing, based at least in part on contact between the sidewall and the skull, an acceleration of current drawn by the drill motor to meet or exceed the triggering threshold at or after penetration of the cutting tip through the skull.

30. The method of any of examples 25-29 wherein the triggering threshold includes a value of the parameter associated with penetration of the drill bit through the skull, and wherein causing the drill motor to stop the rotation of the drill bit includes causing the drill motor to stop the rotation of the drill bit when the parameter meets or exceeds the value.

31. The method of any of examples 25-30 wherein the parameter is a first parameter and the triggering threshold is a first triggering threshold, and wherein the method further comprises causing the drill motor to stop the rotation of the drill bit when a second parameter of the drill motor meets or exceeds a second triggering threshold.

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, any of the features of the drilling systems described herein may be combined with any of the features of the other drilling systems described herein and vice versa. Moreover, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions associated with drilling systems have not been shown or described in detail to avoid unnecessarily obscuring the description of the embodiments of the technology. Where the context permits, singular or plural terms may also include the plural or singular term, respectively.

Unless the context clearly requires otherwise, throughout the description and the examples, the words “comprise,” “comprising,” and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A surgical drilling device comprising:

a drill bit having a cutting surface, wherein at least a portion of the cutting surface is configured to remain in contact with a tissue of a patient when in operation;

a drill motor operably coupled to the drill bit, wherein the drill motor is configured to generate a parameter when in operation, and wherein the parameter is associated with the cutting surface and includes a measure of current drawn by the drill motor when in operation;

a sensing element configured to detect the parameter; and a processor operably coupled to the drill motor and the sensing element and configured to perform operations comprising obtaining, via the sensing element, multiple drill motor current values during a drilling procedure;

determining a first derivative of the multiple drill motor current values by obtaining a difference between individual ones of the multiple drill motor current values;

determining a second derivative of the drill motor current values by obtaining a difference between individual ones of the first derivative of the multiple drill motor current values; and when the second derivative meets or exceeds a triggering threshold, causing the drill motor to slow, stop, and/or reverse and thereby slow, stop, and/or reverse rotation of the drill bit.

2. The surgical drilling device of claim 1 wherein the cutting surface is configured to cause an increase in the parameter when the drill bit penetrates through the tissue.

3. The surgical drilling device of claim 1 wherein the cutting surface is configured to cause the parameter to meet or exceed the triggering threshold when the drill bit penetrates through the tissue.

4. The surgical drilling device of claim 1 wherein the cutting surface includes a tapered sidewall, wherein the drill bit further includes a cutting tip, and wherein the tapered sidewall is configured to cause the second derivative of the drill motor current to meet or exceed the triggering threshold at or after penetration of the cutting tip through the tissue.

5. The surgical drilling device of claim 1 wherein the cutting surface includes a sidewall of the drill bit.

6. The surgical drilling device of claim 5 wherein at least a portion of the sidewall is configured to maintain contact with the tissue after the drill bit has penetrated through the tissue.

7. The surgical drilling device of claim 5 wherein the sidewall is tapered relative to a longitudinal axis of the drill bit.

8. The surgical drilling device of claim 5 wherein the sidewall is at an angle of between about 1 degree and about 15 degrees relative to a longitudinal axis of the drill bit.

9. The surgical drilling device of claim 5 wherein the drill bit further includes a cutting tip at a distal end of the drill bit, wherein the sidewall extends proximally from the cutting tip.

10. The surgical drilling device of claim 9 wherein the sidewall is angled radially outward and in a proximal direction from the cutting tip.

11. The surgical drilling device of claim 9 wherein the triggering threshold includes a value of the parameter associated with penetration of the cutting tip through the tissue.

12. The surgical drilling device of claim 1 wherein the drill bit further includes a flute extending in a direction parallel to a longitudinal axis of the drill bit.

13. The surgical drilling device of claim 12 wherein the flute has a linear shape.

14. The surgical drilling device of claim 1 wherein the sensing element includes an analog-to-digital converter.

15. The surgical drilling device of claim 1 wherein the parameter further includes at least one of a drill motor voltage, a drill motor torque, a drill motor resistance to torque, a drill bit cutting lip contact, a drill bit feed rate, and/or a normal force applied to the drill bit.

16. The surgical drilling device of claim 1 wherein the parameter is a first parameter and the triggering threshold is a first triggering threshold, wherein the drill motor is configured to generate a second parameter when in operation, and wherein the processor is further configured to cause the drill motor to slow, stop, and/or reverse to thereby slow, stop, and/or reverse the rotation of the drill bit when the second parameter meets or exceeds a second triggering threshold.

17. One or more non-transitory computer readable media having instructions stored thereon that, when executed by one or more processors of a drilling system, cause the drilling system to perform operations comprising:

providing power to a drill motor to cause rotation of a drill bit of the drilling system, wherein the drill bit includes a cutting surface, and wherein at least a portion of the cutting surface is configured to contact a tissue of a patient when in operation;

determining, via a sensing element of the drilling system, a parameter of the drill motor including a drill motor current, wherein the parameter corresponds to a shape of the cutting surface, and wherein determining the parameter includes determining a second derivative of the drill motor current by steps comprising obtaining multiple drill motor current values during a drilling procedure;

determining a first derivative of the multiple drill motor current values by obtaining a difference between individual ones of the multiple drill motor current values; and determining the second derivative of the drill motor current by obtaining a difference between individual ones of the first derivative of the multiple drill motor current values; and when the parameter meets or exceeds a triggering threshold, causing the drill motor to slow, stop, and/or reverse the rotation of the drill bit.

18. The one or more non-transitory computer readable media of claim 17, the operations further comprising causing, based at least in part on contact between the cutting surface and the tissue at or near penetration of the drill bit through the tissue, an increase in the parameter when the drill bit penetrates through the tissue.

19. The one or more non-transitory computer readable media of claim 17, the operations further comprising causing, based at least in part on contact between the cutting surface and the tissue, the parameter to meet or exceed the triggering threshold when the drill bit penetrates through the tissue.

20. The one or more non-transitory computer readable media of claim 17 wherein the cutting surface includes a tapered sidewall and the drill bit further includes a cutting tip, the operations further comprising causing, based at least in part on contact between the sidewall and the tissue, an acceleration of current drawn by the drill motor to meet or exceed the triggering threshold at or after penetration of the cutting tip through the tissue.

21. The one or more non-transitory computer readable media of claim 17 wherein the triggering threshold includes a value of the parameter associated with penetration of the drill bit through the tissue, and wherein causing the drill motor to slow, stop, and/or reverse the rotation of the drill bit includes causing the drill motor to stop the rotation of the drill bit when the parameter meets or exceeds the value.

22. The one or more non-transitory computer readable media of claim 17 wherein the parameter is a first parameter and the triggering threshold is a first triggering threshold, and wherein the instructions are further configured to cause the drill motor to slow, stop, and/or reverse the rotation of the drill bit when a second parameter of the drill motor meets or exceeds a second triggering threshold.

23. A method of operating a surgical drilling device, comprising:

providing power to a drill motor to cause rotation of a drill bit of the surgical drilling device, wherein the drill bit includes a cutting surface, and wherein at least a portion of the cutting surface is configured to contact a tissue of a patient when in operation;

determining, via a sensing element of the surgical drilling device, a parameter of the drill motor, wherein the parameter corresponds to a shape of the cutting surface, wherein determining the parameter includes determining a second derivative of current drawn by the drill motor when in operation by steps comprising obtaining multiple drill motor current values during a drilling procedure;

determining a first derivative of the multiple drill motor current values by obtaining a difference between individual ones of the multiple drill motor current values, and determining the second derivative by obtaining a difference between individual ones of the first derivative of the multiple drill motor current values; and when the parameter meets or exceeds a triggering threshold, causing the drill motor to slow, stop, and/or reverse the rotation of the drill bit.

24. The method of claim 23 wherein causing the drill motor to slow, stop, and/or reverse includes causing the drill motor to slow, stop, and/or reverse based at least in part on an increase in the parameter when the drill bit penetrates through the tissue.

25. The method of claim 23, further comprising causing, based at least in part on contact between the cutting surface and the tissue, the parameter to meet or exceed the triggering threshold when the drill bit penetrates through the tissue.

26. The method of claim 23, wherein the cutting surface includes a tapered sidewall and the drill bit further includes a cutting tip, further comprising causing, based at least in part on contact between the sidewall and the tissue, an acceleration of current drawn by the drill motor to meet or exceed the triggering threshold at or after penetration of the cutting tip through the tissue.

27. The method of claim 23 wherein the triggering threshold includes a value of the parameter associated with penetration of the drill bit through the tissue, and wherein causing the drill motor to slow, stop, and/or reverse the rotation of the drill bit includes causing the drill motor to slow, stop, and/or reverse the rotation of the drill bit when the parameter meets or exceeds the value.

28. The method of claim 23 wherein the parameter is a first parameter and the triggering threshold is a first triggering threshold, and wherein the method further comprises causing the drill motor to slow, stop, and/or reverse the rotation of the drill bit when a second parameter of the drill motor meets or exceeds a second triggering threshold.

29. The surgical drilling device of claim 1 wherein the processor is further configured to filter data detected via the sensing element and associated with the parameter.

30. The surgical drilling device of claim 29 wherein the processor includes control electronics comprising a low-pass filter.

31. The surgical drilling device of claim 1 wherein the tissue includes skull bone tissue of the patient and wherein at least a portion of the cutting surface is configured to remain in contact with the skull bone tissue when in operation.

32. The one or more non-transitory computer readable media of claim 17 wherein:

determining the parameter comprises:

obtaining, via the sensing element, data associated with the parameter, and filtering the data; and the operations further comprise comparing the filtered data to the triggering threshold.

33. The one or more non-transitory computer readable media of claim 32 wherein filtering the data includes low-pass filtering the data.

34. The one or more non-transitory computer readable media of claim 17 wherein the tissue includes skull bone tissue of the patient and wherein at least a portion of the cutting surface is configured to remain in contact with the skull bone tissue when in operation.

35. The method of claim 23 wherein:

determining the parameter comprises:

obtaining, via the sensing element, data associated with the parameter, and filtering the data; and the method further comprises comparing the filtered data to the triggering threshold.

36. The method of claim 35 wherein filtering the data includes low-pass filtering the data.

37. The method of claim 23 wherein the tissue includes skull bone tissue of the patient and wherein at least a portion of the cutting surface is configured to remain in contact with the skull bone tissue when in operation.

* * * * *